United States Patent
Lee

(10) Patent No.: US 7,046,762 B2
(45) Date of Patent: *May 16, 2006

(54) SYSTEMS AND METHODS FOR GLOBAL OPTIMIZATION OF TREATMENT PLANNING FOR EXTERNAL BEAM RADIATION THERAPY

(75) Inventor: Eva K. Lee, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 36 days.

This patent is subject to a terminal disclaimer.

(21) Appl. No.: 10/742,471

(22) Filed: Dec. 18, 2003

(65) Prior Publication Data

US 2004/0165696 A1    Aug. 26, 2004

Related U.S. Application Data

(63) Continuation-in-part of application No. 10/341,257, filed on Jan. 13, 2003, now Pat. No. 6,741,674, which is a continuation of application No. 09/706,915, filed on Nov. 6, 2000, now Pat. No. 6,546,073.

(60) Provisional application No. 60/433,657, filed on Dec. 18, 2002, provisional application No. 60/164,029, filed on Nov. 5, 1999.

(51) Int. Cl.
*A61N 5/10* (2006.01)

(52) U.S. Cl. .................................. 378/65; 378/901

(58) Field of Classification Search ............. 378/64, 378/65, 901
See application file for complete search history.

(56) References Cited

U.S. PATENT DOCUMENTS

| | | | |
|---|---|---|---|
| 5,027,818 A | 7/1991 | Bova et al. | 600/427 |
| 5,373,844 A | 12/1994 | Smith et al. | 600/427 |
| 5,458,125 A | 10/1995 | Schweikard | 600/407 |
| 5,555,283 A | 9/1996 | Shiu et al. | 378/151 |
| 5,602,892 A | 2/1997 | Llacer | 378/65 |
| 5,748,700 A | 5/1998 | Shepherd et al. | 378/65 |
| 5,815,547 A | 9/1998 | Shepherd et al. | 378/65 |

(Continued)

OTHER PUBLICATIONS

Langer, M.; Lee, E.K.; Deasy, J.O.; Rardin, R.L.; and Deye, J.A.; "*Operations Research Applied to Radiotherapy, an NCI-NSF-Sponsored Workshop*—Feb. 7-9, 2002," Int. J. Radiation Oncology Biol. Phys., vol. 57, No. 3; 2003; pp. 762-768.

(Continued)

*Primary Examiner*—David V Bruce
(74) *Attorney, Agent, or Firm*—Thomas, Kayden, Horstemeyer & Risley, LLP

(57) ABSTRACT

Systems and methods for providing an optimal treatment plan for delivering a prescribed radiation dose to a predefined target volume within a patient using an external beam radiation delivery unit are provided. One such method comprises: receiving information corresponding to at least one parameter related to intensity-modulated radiation therapy (IMRT) to be used in developing the optimal treatment plan; receiving information corresponding to at least one clinical objective related to a target volume and a critical structure; developing a treatment plan optimization model based on a plurality of variables corresponding to the at least one parameter related to IMRT and the at least one clinical objective which define a global system; and developing a globally optimal treatment plan which optimizes the at least one clinical objective subject to the at least one parameter.

26 Claims, 18 Drawing Sheets

U.S. PATENT DOCUMENTS

| | | | |
|---|---|---|---|
| 5,879,281 A | 3/1999 | Ein-Gal | 600/1 |
| 5,945,684 A | 8/1999 | Lam et al. | 250/492.3 |
| 6,044,126 A | 3/2000 | Rousseau et al. | 378/65 |
| 6,260,005 B1 | 7/2001 | Yang et al. | 703/11 |
| 6,546,073 B1 | 4/2003 | Lee | 378/65 |
| 6,741,674 B1 * | 5/2004 | Lee | 378/65 |

OTHER PUBLICATIONS

Lee, E.K.; Fox, T.; and Crocker, I.; "*Integer Programming Applied to Intensity-Modulated Radiation Therapy Treatment Planning*," Kluwer Academic Publishers; 2002; pp. 1-19.

Lee, E.K.; "*Optimization with Multiple Objectives*," slideshow prepared for the NCI-NSF workshop on Operations Research in Radiation Therapy; Feb. 2002; 17 pages.

Fippel, M.; Alber, M.; Birkner, M; Laub, W.; Nüsslin, F.; and Kawrakow, I.; "*Inverse Treatment Planning for Radiation Therapy Based on Fast Monte Carlo Dose Calculation*," Advanced Monte Carlo for Radiation Physics, Particle Transport Simulation and Applications: Proceedings of the Monte Carlo 2000 Conference; 2000; pp. 217-222.

\* cited by examiner

Global Optimization of Treatment Planning: Operator Interface

Input Dose and Clinical Parameters

| Anatomical Structures | | Voxels (cm³) | PrDose (cGy) | Lower Bound Factor | Upper Bound Factor |
|---|---|---|---|---|---|
| Tumor | Prostate | 211.4 | 7560 | 0.95 | 1.05 |
| Critical Structures | Rectum | 64.3 | - | 0 | 1.05 |
| | Bladder | 353.2 | - | 0 | 1.00 |
| Norm. Tissue | Skin | - | - | 0 | <= 30% receives >= 0.95 |

Coverage  >= 95%

Homogeneity  <= 1.3 # of Input Candidate Beams  40 # of Output Beams  7

SUBMIT    CLEAR

FIG. 7

Global Optimization of Treatment Planning: Operator Interface

Input Dose and Clinical Parameters

| PRESCRIPTION DATA | DOSE VOLUME CONSTRAINTS | CLINICAL OBJECTIVE |
|---|---|---|
| Prostate surface and uniformity points | Prostate: 97% of volume should receive 7560 cGy | Minimize dose to bladder and rectum while achieving dose to prostate. Maintain dose to prostate volume within 10% of prescription dose (i.e., no hot spots.) |
| Rectum surface points | Rectum surface: 30% of surface points can receive up to 7560 cGy | |
| Bladder surface points | Rectum surface: 60% of surface <= 4050 cGy | PHYSICAL CONSTRAINTS |
| Dilation 30 mm from prostate surface - surface points | Bladder surface: 60% of surface receive <=.4050 cGy | Use fewer than 7 beams |
| Dilation 60 mm from prostate surface - surface points | Dilation_30mm: no limits but can use it to keep dose low in this area | SUBMIT   CLEAR |
| | Dilation_60mm: no limits but can use it to keep dose low in this area | |

*FIG. 8*

SYSTEMS AND METHODS FOR GLOBAL OPTIMIZATION OF TREATMENT PLANNING FOR EXTERNAL BEAM RADIATION THERAPY

CROSS-REFERENCE TO RELATED APPLICATIONS

This application is a continuation-in-part application of U.S. Utility Application entitled "Systems and Methods for Global Optimization of Treatment Planning for External Beam Radiation Therapy," having Ser. No. 10/341,257, filed Jan. 13, 2003, now U.S. Pat. No. 6,741,674, which is a continuation application of U.S. Utility Application entitled "Systems and Methods for Global Optimization of Treatment Planning for External Beam Radiation Therapy," having Ser. No. 09/706,915, filed Nov. 6, 2000 (now U.S. Pat. No. 6,546,073 B1), which claims priority to U.S. Provisional Application entitled "Systems and Methods for Global Optimization of Treatment Planning for External Beam Radiation Therapy," having Serial No. 60/164,029, filed Nov. 5, 1999, each of which are entirely incorporated herein by reference. This application also claims priority to U.S. Provisional Application No. 60/433,657, filed Dec. 18, 2002, which is entirely incorporated herein by reference.

TECHNICAL FIELD

The present invention relates generally to treatment planning for external beam radiation therapy, and more particularly, to systems and methods for global optimization of treatment planning for external beam radiation therapy.

BACKGROUND

External beam radiation therapy is a well-known treatment option available to the radiation oncology and neurosurgery communities for treating and controlling certain central nervous systems lesions, such as arteriovenous malformations, metastatic lesions, acoustic neuromas, pituitary tumors, malignant gliomas, intracranial tumors, and tumors in various parts of the body (e.g., lung, breast, prostate, pancreas, etc.). As the name implies, the procedure involves the use of external beams of radiation directed into the patient at the lesion using either a gamma unit (referred to as a Gamma Knife), a linear accelerator, or similar beam delivery apparatus. Although treating the lesions with the radiation provides the potential for curing the related disorder, the proximity of critical normal structures and surrounding normal tissue to the lesions makes external beam radiation therapy an inherently high risk procedure that can cause severe complications. Hence, the primary objective of external beam radiation therapy is the precise delivery of the desired radiation dose to the target area defining the lesion, while minimizing the radiation dose to surrounding normal tissue and critical structures.

The process of treating a patient using external beam radiation therapy consists of three main stages. First, a precise three-dimensional map of the anatomical structures in the location of interest (target volume) is constructed using any conventional three-dimensional imaging technology, such as computed tomography (CT) or magnetic resonance imaging (MRI). Second, a treatment plan is developed for delivering a predefined dose distribution to the target volume that is acceptable to the clinician. Finally, the treatment plan is executed using an accepted beam delivery apparatus.

Thus, the basic strategy of external beam radiation therapy is to utilize multiple beams of radiation from multiple directions to "cross-fire" at the target volume. In that way, radiation exposure to normal tissue is kept at relatively low levels, while the dose to the tumor cells is escalated. Thus, the main objective of the treatment planning process involves designing a beam profile, for example, a collection of beams, that delivers a necrotic dose of radiation to the tumor volume, while the aggregate dose to nearby critical structures and surrounding normal tissue is kept below established tolerance levels.

One existing method for treatment planning in external beam radiation therapy is standard manual planning. This method is referred to as forward planning because the physician solves the direct problem of determining the appropriate dose distribution given a known set of beam characteristics and beam delivery parameters. In other words, standard manual planning involves a trial-and-error approach performed by an experienced physician. The physician attempts to create a plan that is neither complex nor difficult to implement in the treatment delivery process, while approximating the desired dose distribution to the greatest extent possible. For instance, the physician may choose how many isocenters to use, as well as the location in three dimensions, the collimator size, and the weighting to be used for each isocenter. A treatment planning computer may calculate the dose distribution resulting from this preliminary plan. Prospective plans are evaluated by viewing isodose contours superimposed on anatomical images and/or with the use of quantitative tools such as cumulative dose-volume histograms (DVH's).

Standard manual planning has many disadvantages. This iterative technique of plan creation and evaluation is very cumbersome, time-consuming, and far from optimal. Thus, manual planning results in much higher costs for patients and insurers. The physician or other experienced planner can evaluate only a handful of plans before settling on one. Thus, standard planning has very limited success in improving local tumor control or reducing complications to normal tissue and critical structures, and as a result, greatly limits the quality-of-life for patients. In standard manual planning, there is no mechanism for allowing the advance imposition of clinical properties, such as, for example, an upper bound on dose received by normal tissue or the specific shape of dose-response curves to the tumor and to critical structures, on the resulting plans. Furthermore, manual planning is subjective, inconsistent, far from optimal, and only enables a small amount of treatment plans to be examined by the physician.

Another method for treatment planning in external beam radiation therapy employs computer systems to optimize the dose distributions specified by physicians based on a set of preselected variables. This approach is known as inverse planning in the medical community because the computer system is used to calculate beam delivery parameters that best approximate the predetermined dose, given a set of required doses, anatomical data on the patient's body and the target volume, and a set of preselected or fixed beam orientation parameters and beam characteristics. In order to solve the complex problem of arriving at an optimal treatment plan for the domain of possible variables, all existing methods of inverse treatment planning fix at least a subset of the set of variables. For example, a particular modality of external beam radiation therapy may include the following domain of possible variables: (1) number of beams, (2) configuration of beams, (3) beam intensity, (4) initial gantry angle, (5) end gantry angle, (6) initial couch angle, (7) end couch angles, (8) prescription dose, (9) target volume, and (10) set of target points. State of the art inverse treatment planning approaches preselect a subset of these variables and fix them during the optimization calculation.

Despite its obvious advantages over the standard manual approach, existing inverse treatment planning approaches have several disadvantages and inadequacies. As described above, these approaches do not incorporate each of the domain of possible variables into the optimization calculation. Instead, these approaches fix at least a subset of these variables to arrive at an "optimal" treatment plan. This type of "local optimization" is inherently problematic because it does not allow the full flexibility of choosing different beam geometries, beam orientation parameters, and beam parameters, imposing dose limits, and placing constraints on physical planning parameters. In other words, these approaches do not enable "global optimization" of treatment planning for external beam radiation therapy. Therefore, these approaches are limited by "less than optimal" treatment plans and, consequently, are unable to adequately control tumor growth or reduce normal tissue complications. Furthermore, there are an infinite number of possible treatment plans in inverse treatment planning, and existing methods only look at a small subset of potential plans and select the "best" from the subset. Thus, the resulting treatment plan is not a globally optimal plan.

Furthermore, existing inverse treatment planning are not well-suited for use with newer external beam radiation therapy modalities. Recent technological advances have resulted in sophisticated new devices and procedures for external beam radiation delivery, such as, for example, high-resolution multi-leaf collimators, intensity-modulated modulated radiation therapy (IMRT), and non-coplanar arc stereotactic radiosurgery (NASR). Unlike conventional radiation therapy where radiation profiles are altered via the use of a limited number of wedges, beam blocks and compensating filters, these new devices and procedures allow a large collection of beams to be shaped in any desired fashion with regard to both the geometrical shape and fluence across the field to create fixed or moving nonuniform beams of photons or charged particles. While the flexibility and precise delivery capability resulting from these advances is clearly advantageous, their full potential cannot be realized using "local optimization" schemes which do not incorporate each of the domain of possible variables into the optimization calculation, but instead fix at least a subset of these variables to arrive at an "optimal" treatment plan.

Thus, an unaddressed need exists in the industry to address the aforementioned deficiencies and inadequacies.

SUMMARY

The present invention solves the problems described above by providing systems and methods for providing a globally optimal treatment plan for delivering a prescribed radiation dose to a target tumor volume within a patient using an external beam radiation source. The present invention enables a physician performing external beam radiation therapy to develop a globally optimal treatment plan, which results in improved patient care and improved efficiency. For example, in the field of external beam radiation therapy, the present invention reduces normal tissue complications, improves tumor control, enables physicians to evaluate a set of globally optimal solutions, reduces the time and cost associated with producing a treatment plan, eliminates trial and error visual optimization, enables physicians to perform radiation therapy in complex situations, such as where critical structures are near the tumor, improves the percentage of tumor volume covered by a prescription isodose line, reduces the ratio of the maximum dose to the prescribed dose, improves the ratio of the volume of the prescribed isodose surface to the target volume, and improves the ratio of the maximum dose received by normal tissue to the prescribed dose.

Briefly described, the systems according to the present invention for providing an optimal treatment plan have three main components. The systems have a user interface for enabling a user to specify at least one parameter related to IMRT, at least one constraint, and at least one clinical objective; a treatment plan modeling module configured to develop a treatment plan optimization model containing a plurality of variables corresponding to the at least one parameter related to IMRT, the at least one constraint, and the at least one clinical objective; and a global optimization module configured to calculated a globally optimal treatment plan which optimizes the at least one clinical objective subject to the at least one parameter related to IMRT and the at least one constraint. The systems may also include a visual evaluation functionality which is adapted to display information related to the optimal treatment plan to a physician.

The present invention can also be viewed as providing methods for providing an optimal treatment plan for delivering a prescribed radiation dose to a predefined target volume within a patient using an external beam radiation delivery unit. Briefly, one such method involves receiving information corresponding to at least one parameter related to intensity-modulated radiation therapy (IMRT) to be used in developing the optimal treatment plan: receiving information corresponding to at least one clinical objective related to a target volume and a critical structure; developing a treatment plan optimization model based on a plurality of variables corresponding to the at least one parameter related to IMRT and the at least one clinical objective which define a global system: and developing a globally optimal treatment plan which optimizes the at least one clinical objective subject to the at least one parameter.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The systems and methods according to the present invention can be better understood with reference to the following drawings.

FIG. 7 is a screenshot of another embodiment of a user input screen supported by the user interface of FIG. 5 for enabling a user to designate various dose and clinical parameters for IMRT treatment planning.

FIG. 8 is a screenshot of another embodiment of a user input screen supported by the user interface of FIG. 5 for enabling a user to designate various dose and clinical constraints and objectives for IMRT treatment planning.

DETAILED DESCRIPTION

Figure 1:
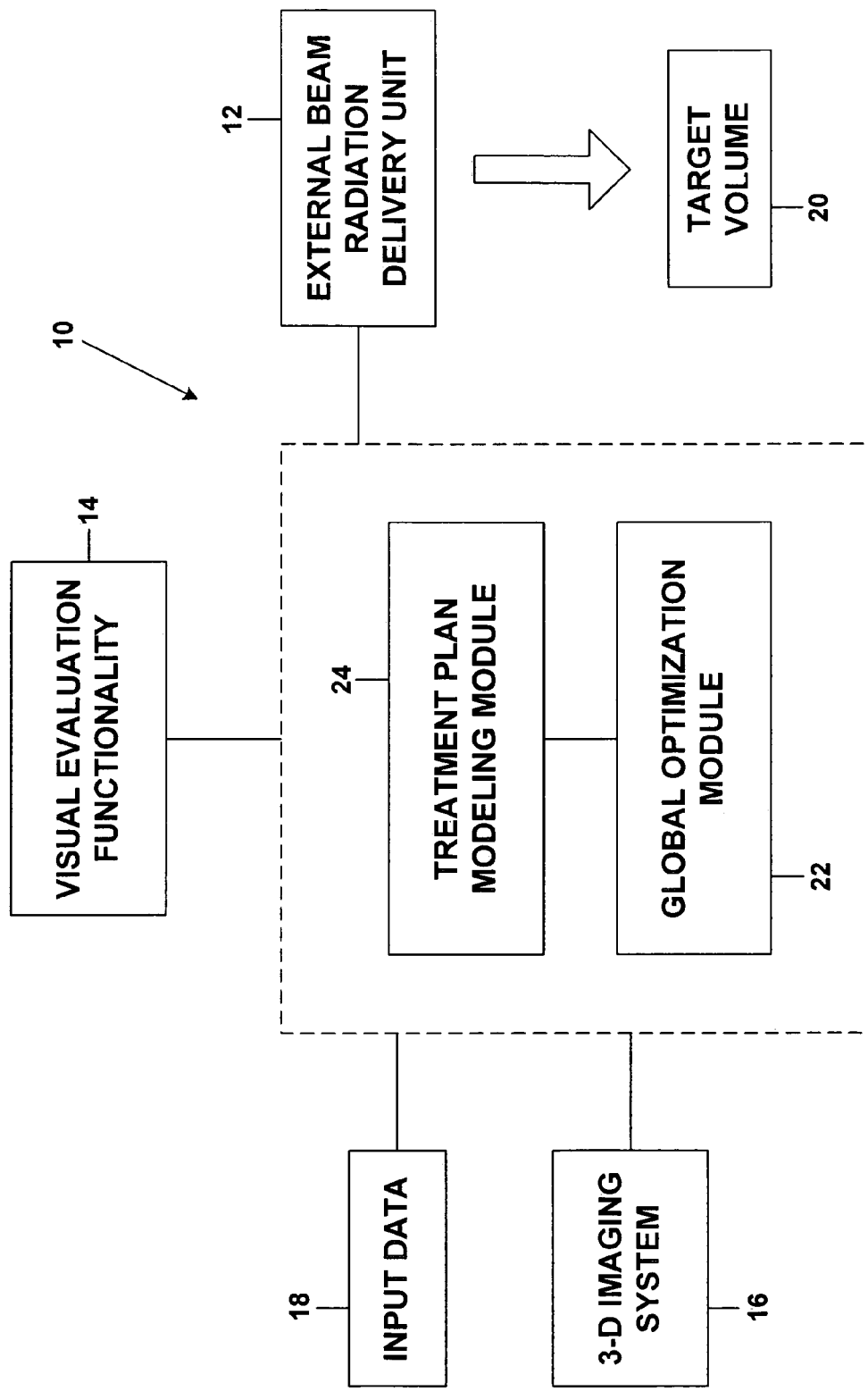
FIG. 1 is a functional block diagram of one embodiment of a system according to the present invention.

Having summarized the invention above, reference is now made in detail to the description of the invention as illustrated in the drawings. While the invention will be described in connection with these drawings, there is no intent to limit it to the embodiment or embodiments disclosed. On the contrary, the intent is to cover all alternatives, modifications and equivalents included within the spirit and scope of the invention as defined by the appended claims.

System Overview

FIG. 1 illustrates a functional block diagram of a preferred embodiment of a system 10 according to the present invention for enabling global optimization of treatment planning for external beam radiation therapy. System 10 is connected to an external beam delivery unit 12, visual evaluation functionality 14, and three-dimensional imaging system 16.

External beam delivery unit 12 may be any conventional equipment used in external beam radiation therapy for delivering doses of radiation to a target volume 20 within a patient, such as, for example, a linear accelerator (LINAC), a Gamma Knife, or any other external device capable of providing a radiation source. External beam delivery unit 12 may comprise a plurality of external beams having variable intensity, a plurality of collimators for adjusting the size of the beams, and a mechanism for moving the unit with respect to a patient positioned within a stereotactic frame in order to adjust the angle and entry point of each radiation beam.

System 10 also contemplates using various radiation modalities with external beam delivery unit 12. For example, system 10 may be used with static conformal radiation therapy (SCRT), non-coplanar arc stereotactic radiosurgery (NASR), intensity modulated radiation therapy (IMRT), and intensity modulated arc therapy (IMAT).

SCRT involves the use of three-dimensional computer planning systems to geometrically shape the radiation field to ensure adequate coverage of the target, while sparing normal tissue. The tools for SCRT include patient-specific CT data, beam's-eye-view (BEV) treatment planning, and multileaf collimators (MLC). Guided by the target contours identified in the CT images, beam orientations are chosen and beam apertures are accurately delineated using BEV. The beam aperture can be fabricated with conventional blocks or defined by MLC. The dose distribution within the field is determined by choice of beam intensity and simple modulators such as wedges and tissue compensators.

NASR is a technique used for treating brain tumors. Radiosurgery is distinguished from conventional external beam radiation therapy of the central nervous system by its localization and treatment strategy. In radiosurgery, the target volume of tissue is much smaller (tumors 10–35 mm in diameter), the number of fractions (treatment sessions) is much less, and the dose per fraction is much larger than in conventional radiotherapy. Radiosurgery involves the use of external beams of radiation guided to a desired point within the brain using a precisely calibrated stereotactic frame mechanically fixed to the head, a beam delivery unit, such as a LINAC Gamma Knife, and three-dimensional medical imaging technology. For LINAC radiosurgery, the table on which the patient lies and the beam delivery unit are capable of rotating about distinct axes in order to adjust the angle and entry point of a radiation beam. The tissue affected by each beam is determined by the patient's position within the stereotactic frame, by the relative position of the frame in relation to the beam delivery unit, by collimators that adjust the size of the beam, and by the patient's anatomy. Additionally, the intensity of each beam can be adjusted to govern its dose contribution to each point.

IMRT is a recently developed treatment modality in radiotherapy. In IMRT the beam intensity is varied across the treatment field. Rather than being treated with a single, large, uniform beam, the patient is treated instead with many very small beams, each of which can have a different intensity. When the tumor is not well separated from the surrounding organs at risk—such as what occurs when a tumor wraps itself around an organ—there may be no combination of uniform intensity beams that will safely separate the tumor from the healthy organ. In such instances, adding intensity modulation allows more intense treatment of the tumor, while limiting the radiation dose to adjacent healthy tissue.

IMAT is a form of IMRT that involves gantry rotation and dynamic multileaf collimation. Non-coplanar or coplanar arc paths are chosen to treat the target volume delineated from CT images. The arcs are chosen such that intersecting a critical structure is avoided. The fluence profiles at every 5 degrees are similar to a static IMRT field. As the gantry rotates, the dynamic MLC modulates the intensity to deliver the dose to the target volume while sparing normal tissue. The large number of rotating beams may allow for a more conformal dose distribution than the approach of multiple intensity modulated beams.

Thus, the systems and methods of the present invention are not limited to a particular type of external beam delivery unit 12 or a particular modality, but instead may employ any type of external beam delivery unit or radiation modality.

Visual evaluation functionality 14 may be any conventional imaging module adapted to interface with system 10 and capable of visually displaying an optimal treatment plan for delivering radiation to a patient using external beam delivery unit 12. Visual evaluation functionality 14 may be a computer monitor, a television monitor, any type of printout from a computer, or any other imaging module used by physicians to evaluate the effectiveness of a particular treatment plan for a patient. For example, visual evaluation functionality 14 may be configured to enable physicians to view dose-volume histograms and isodose surfaces for a treatment plan overlayed with a diagram of the target volume and surrounding areas, including normal surrounding tissue and critical structures.

Three-dimensional imaging system 16 may be any three-dimensional imaging technology used to delineate target volume 20 of a tumor or similar region within a patient, such as, for example, a computed tomography (CT) system, a magnetic resonance imaging (MRI) system, or any similar system. It should be understood by skilled persons in the art that there are many ways to capture images of lesions within a human body, and, therefore, this invention should not be limited to any particular type of imaging system. The important aspect is that imaging system 16 is capable of identifying the contours of target volume 20 along with surrounding normal tissues and critical structures.

Figure 2:
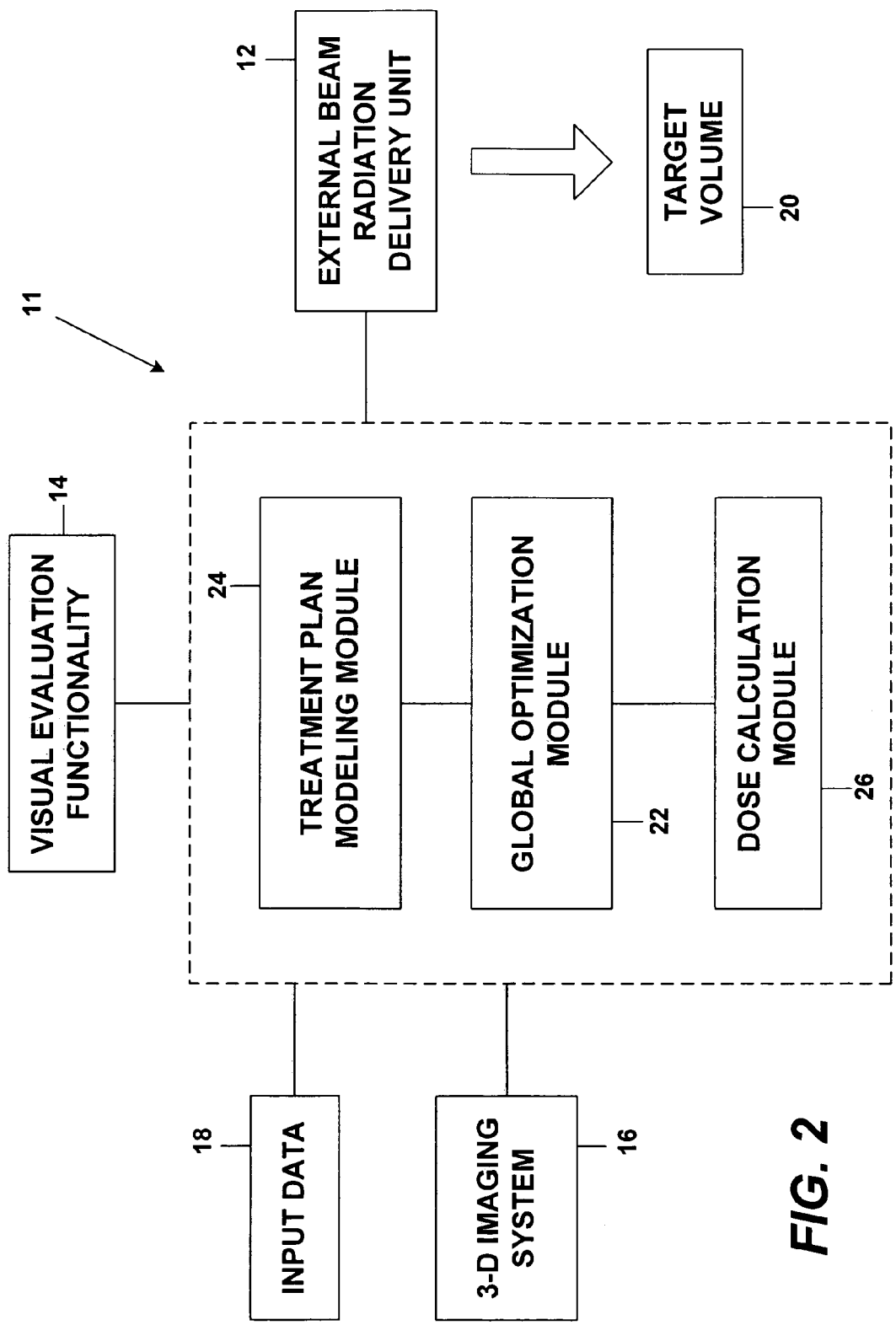
FIG. 2 is a functional block diagram of another embodiment of a system according to the present invention.

As shown in FIG. 1, system 10 comprises two main components: global optimization module 22 and treatment plan modeling module 24. FIG. 2 shows an alternative embodiment of a system 11 according to the present invention. System 11 is similar to system 10 except that it incorporates a third component, dose calculation module 26. Each of these components will be described in detail below.

System Input

Referring again to FIG. 1, system 10 receives various inputs from imaging system 16, as well as input data 18. Although in the preferred embodiment input data 18 represents all information input into system 10 not received from imaging system 16, it should be noted that input data 18 may actually come from any source. For example, input data 18 may be received by system 10 as a manual input by a physician or automatic input via a computer directed by a physician. FIG. 1 is merely illustrating by way of example that system 10 receives information related to target volume 20 via imaging system 16 and that all other input is referred to as input data 18.

Input data 18 to system 10 includes CT and/or MRI images of target volume 20. The contours of target volume 20 and surrounding normal tissue and critical structures are identified and segmented using the medical images. These anatomical contours are used as inputs to system 10. Other inputs include clinical planning information such as prescription dose; target lower and upper bounds on the radiation dose delivered to the tumor volume, nearby healthy tissue, and critical structures; choice of possible isocenters; and desired number of beams, isocenters, and couch angles used in the final physical plan. The anatomical contours and dose calculation points from the imaging coordinate systems are transformed via a coordinate system transformation algorithm to the stereotactic coordinate system. An automated arc selection method employing computational geometry techniques is used to select a representative collection of candidate arcs.

As described above, system 10 is not limited to a particular type of apparatus for external beam delivery unit 12 or a particular modality. Nonetheless, for exemplary purposes, system 10 will be described with respect to a preferred method using LINAC arcing radiosurgery.

In LINAC arcing radiosurgery, the following treatment parameters define an arc: a target point location variable t; collimator size C, gantry initial and end angles $\theta_i$ and $\theta_e$ and couch angle $\phi$. The isocenters for candidate arcs are chosen in 2 mm intervals and reside in the target volume. The candidate arcs vary the couch and gantry angles in 1° increments from −90° to 90° and 0° to 359°, respectively. These candidate beam orientation parameters (couch and gantry angles) are selected so that they match the beam orientations selected by clinicians manually. Twelve circular collimator sizes are applied to the candidate arcs, ranging from 12.5 to 40 mm in 2.5 mm steps. The resulting collection of beams comprise a large set of candidate beams used for instantiating a treatment plan optimization model used by treatment plan modeling processor 24.

Treatment Plan Oiptimization Model/Treatment Plan Modeling Module

As shown in FIG. 1 and mentioned above, system 10 comprises treatment plan modeling module 24 and global optimization module 22. Treatment plan modeling module 24 receives inputs 18, and based on these inputs, creates a treatment plan optimization model. The treatment plan optimization model incorporates every potential variable included within input 18. In other words, the treatment plan optimization model represents a global optimization of every potential variable within the system. As will be described in detail below, upon completion, treatment plan modeling module 24 provides the resulting treatment plan optimization model to global optimization module 22 where an optimal treatment plan is determined based on inputs 18.

A preferred embodiment of a treatment plan optimization model will now be described. Given a collection of selected arcs indexed as $\{1, \ldots, N_A\}$, comprised of target points $\{1, \ldots, N_t\}$ and couch angles $\{1, \ldots, N_\phi\}$ (note that each arc associates with a specified collimator size, gantry initial and end angles, target position, and couch angle), the preferred treatment plan optimization model incorporates non-negative continuous variables to record the intensity used for each arc. If an arc is used, thus indicating that the intensity is greater than zero, then it contributes a certain amount of radiation dosage to each voxel in target volume 20. Thus, once the set of potential arc intensities is specified, the total radiation dose received at each voxel can be modeled. For example, in the preferred treatment plan optimization model, $w_a \geq 0$ denotes the intensity (weight) of arc a. Then the total radiation dose at a voxel P is given by the following expression:

$$\sum_{a=1}^{N_A} D_{P,a} w_a \qquad \text{Equation 1}$$

where $D_{P,a}$ denotes the dose contribution to voxel P from arc a as given by the following expression:

$$D_{P,a} = S(C) \int_{\theta_i}^{\theta_e} \text{TMR}(\theta, \phi_a, \bar{d}_{P,a}, r_{P,a}, C_P) \, \text{OAR}(\theta, \phi_a, \bar{d}_{P,a}, r_{P,a}, C_P) \text{IVSQ}(\theta, \phi_a, \bar{d}_{P,a}, r_{P,a}) d\theta \quad \text{Equation 2}$$

$D_{P,a}$ may be calculated using standard dose calculation tools and merely included with input data 18. As shown in FIG. 2, an alternative embodiment of a system 11 may employ an internal dose calculation module 26 to perform this calculation. Dose calculation module 26 may employ computational geometry and measured dosimetry parameters in a semi-empirical formulation to calculate $D_{P,a}$. For instance, to calculate the dose from a fixed beam, say at a point P in the brain, a ray is formed joining P and a point on the central axis of the radiation beam. Dose calculation module 26 may employ a computation method which uses measured dosimetry parameters obtained from a water phantom. The parameters may include: tissue maximum ratios (TMR), total scatter correction factors (S), inverse square correction (IVSQ), and off-axis ratio (OAR). The depth, d, of tissue penetrated by the central ray of the radiation beam, and the depth, $\bar{d}$, of tissue penetrated by the ray formed by connecting the dose calculation voxel P to the radiation source are computed by a ray tracing method. The distance, r, from the dose calculation voxel to the central ray is also computed. Using the values d, $\bar{d}$, and r, the measured dosimetry parameters are calculated for the point P. The dose per monitor unit deposited by one arc of the gantry is the sum of a set of static beams which approximate this arc. The total dose deposited to a point ($D_{P,a}$) is the summation of the dose over all arcs.

The preferred embodiment of the treatment plan optimization model may also incorporate a variety of desirable constraints. For example, clinically prescribed lower and upper bounds, say $L_P$ and $U_P$, for the radiation dose at voxel P can be incorporated with Equation 1 to form the following dosimetric constraints:

$$\sum_{a=1}^{N_A} D_{P,a} w_a \geq L_P \text{ and } \sum_{a=1}^{N_A} D_{P,a} w_a \leq U_P \quad \text{Equation 3}$$

Note that a is characterized by the target point, couch angles, collimator size, and gantry initial and end angles. Thus, a could be more accurately referred to as $a_{t,C,\theta_i,\theta_e,\phi}$. However, for brevity of notation, subscripts are listed only as needed to enhance clarity.

The preferred embodiment of the treatment plan optimization model may also constrain the characteristics of beam arrangements from external beam delivery unit 12. To control the number of target points specified by the optimal plan, the treatment plan optimization model defines a 0/1 indicator variable $t_j$ to denote if target point j is used or not. The following constraints capture the use of target point j in the resulting plan when an arc with target point j is used.

$$w_{a_j} \leq M_{a_j} t_j \text{ and } \sum_{j=1}^{N_t} t_j \leq T \quad \text{Equation 4}$$

Here, $M_{a_j}$ is a positive constant and can be selected as the largest possible beam intensity among candidate arcs having target point j. The second constraint can then be imposed, where T is the maximum number of target points acceptable by the physician for the particular patient. Although complications from radiosurgery treatments may increase with the number of isocenters, it has been shown that for highly irregular shaped tumor volumes, multiple isocenters may improve the conformity of the high dose region. With current state of the art methods, determining an "optimal" beam configuration with multiple target points is extremely difficult and time consuming. The systems and methods of the present invention enable clinicians to include such constraints within the model to assist in determining an optimal treatment plan.

The preferred embodiment of the treatment plan optimization model may also constrain the number of couch angles, and the number of arcs used in the resulting plan due to the physical requirement of adjusting the equipment to achieve the desired configurations for each round of irradiation. For example, the treatment plan optimization model, may employ 0/1 integer variable $\phi_j$, to model the use of couch angle j, and 0/1 integer variable $\beta_a$ to model the use of arc a. In this manner, when $w_{a_j}$ ($w_a$) is positive, then $\phi_j$ ($\beta_a$) will be set to 1. These constraints may take the following form:

$$w_{a_j} \leq N_{a_j} \phi_j \text{ and } \sum_{j=1}^{N_\phi} \phi_j \leq \Phi \quad \text{Equation 5}$$

$$w_a \leq R_a \text{ and } \sum_{a=1}^{N_a} b_a \leq B \quad \text{Equation 6}$$

where $N_{a_j}$ and $R_a$ are constants and can be chosen as the largest possible intensity emitted from arc a, respectively, and $\Phi$ and B are the maximum number of couch angles allowed and beam configurations desired in the optimal plan, respectively.

In a similar manner, the treatment plan optimization model may also constrain the collimator size and the number of distinct gantry angles used in the resulting plans. In addition, it may also impose a minimum beam intensity for each arc to ensure that the resulting plan is practical. These constraints may be important if, in absence of such restrictions, the optimization system returns plans involving, say, hundreds of distinct configurations. Too many configurations may be physically difficult to manage, and it will be impractical to deliver a very complex plan. The treatment plan optimization model is configured to enable dose calculation module 26 to return a realistic plan which can be carried out in a reasonably easy fashion in the treatment delivery room.

The treatment plan optimization model may also incorporate additional constraints to enforce clinical properties desired for individual patients. A variety of optimization objectives can be incorporated with these constraints to direct the selection of a treatment plan. For example, one possible approach is to find a maximal feasible subsystem among the dosimetric constraints. Clinically, this translates into finding a beam configuration which gives the maximum percentage of tumor volume, critical structure and normal tissue satisfying their respective target dose levels. Due to the proximity of critical structures and the tumor volume, it is not possible to find a beam geometry and intensity which satisfies all the dosimetric constraints given in Equation 3. In this case, the treatment plan optimization model may include an indicator variable incorporated into each constraint to capture whether or not the desired dose bound is achieved.

Alternatively, the treatment plan optimization model may be configured to seek a treatment plan which results in the minimum deviation from the clinical prescription bounds. In this case, continuous variables can be added to the constraints in Equation 3 to measure the deviations from the lower and upper bound for each voxel P.

In the preferred embodiment of the systems and methods of the present invention, the treatment plan optimization model employs a mixed integer programming approach to determine an optimal treatment plan which guarantees 100% coverage to tumor volume while minimizing the dose received by proximal critical structures and/or normal tissue. In particular, instead of providing upper and lower dose bounds, the clinician inputs the desired prescription dose received by the tumor volume. In this embodiment, the treatment plan optimization model formulates the problem as:

Minimize $$\sum_{P \in PTV} f_P$$

Subject to the constraints:

$$\sum_{a=1}^{N_A} D_{P,a} w_a - f_P = PRDOSE \quad P \in PTV$$

$$w_{a_j} \leq M_{a_j} t_j \quad a_j \in \{1, \ldots, N_A\}, j \in \{1, \ldots, N_t\}$$

$$\sum_{j=1}^{N_t} t_j \leq T$$

$$w_{a_j} \leq N_{a_j} \phi_j \quad a_j \in \{1, \ldots, N_A\}, j \in \{1, \ldots, N_\phi\}$$

$$\sum_{j=1}^{N_\phi} \phi_j \leq \Phi$$

$$w_a \leq R_a b_a \quad a \in \{1, \ldots, N_A\}$$

$$\sum_{a=1}^{N_A} b_a \leq B$$

$$w_a, f_P \geq 0; t_j, \phi_j, b_a \in \{0, 1\}$$

Equation 7

In Equation 7, PRDOSE is the clinical prescription dose for the predefined tumor volume PTV, T is the maximum number of target points desired by the physicians for the particular patient, and $\Phi$ and B are the maximum number of couch angles allowed and beam configurations desired in the optimal plan, respectively. As described above, $M_{a_j}$, $N_{a_j}$, and $R_a$ are positive constants and can be chosen as the largest intensity possible emitted from a single arc. In Equation 7, the variable $f_P$ denotes the amount of irradiation exceeding the prescription dose at point P. Since $f_P$ is nonnegative, the dose calculation model ensures that point P will receive at least the prescription dose. For points P on the tumor surface, which separates the tumor volume from the normal tissue, in addition to measuring the excess radiation to the tumor surface, $f_P$ can also be viewed as a measure of radiation to the immediately surrounding normal tissue. Minimizing the sum of the variables $f_P$ has the effect of providing a uniform dose distribution on the tumor volume while producing a steep dose gradient outside of the tumor volume. Thus, even in the absence of a critical structure constraining the treatment plan, the dose calculation model ensures that proximal normal tissues receive minimal dose due to rapid dose fall-off.

Global Optimization Module

Global optimization module 22 receives the treatment plan optimization model from treatment plan modeling module 24 and input 18. Based on this information, global optimization module 22 solves instances of the treatment plan optimization model. In the preferred embodiment, a classical branch-and-bound approach is used to determine a true global optimal solution. Moreover, the "intelligent" search mechanism of the branch-and-bound method enables large sections of the solution space to be eliminated from consideration—knowing that no solution within can be optimal—without actually examining each solution within.

The branch-and-bound is a tree search approach where, at each node of the tree, certain binary variables are fixed to zero or one, and the remaining binary variables are relaxed (i.e., allowed to assume any value between zero and one). This results in a linear program (LP) being associated with each node of the tree. The LP at the root node is simply the original 0/1 mixed integer programming (MIP) instance with all of the binary variables relaxed. The tree is constructed such that the binary variables fixed in a parent node will be fixed identically in any of its children, and each child will have an additional binary variable fixed to zero or one. Typically, children are formed in pairs as follows. Assume that the LP at a given node is solved, and one or more of the relaxed binary variables is fractional in the optimal solution. One selects such a fractional binary variable and branches on it. In other words, two child nodes are formed; one with the selected binary variable fixed to zero, and the other with the selected binary variable fixed to one. Of course, each child also inherits all of the fixed binary variables of its parent. Note that the objective value of a child node can be no smaller (in the case of minimization) than the objective value of its parent.

If the linear program at a given node is solved and the optimal solution happens to have integral values for all the relaxed binary variables, then this solution is feasible for the original 0/1 mixed integer program. Once a feasible solution for the original problem is found, the associated objective value can be used as an upper bound (in the case of minimization) for the objective values of LP's at other nodes. In particular, if an LP at another node is solved, and its objective value is greater than or equal to the upper bound, then none of its children could yield a feasible solution for the original MIP with a smaller objective value than the one already obtained. Hence, no further exploration of this other node is needed, and the node is said to be fathomed.

Two other criteria for fathoming a node are apparent: if the associated LP is infeasible, or if the optimal solution of the LP has integral values for all relaxed binary variables, then no further exploration of the node is required. In the latter case, the optimal objective value of the LP will be compared with the current upper bound, and the upper bound will be updated if needed. The tree search ends when all nodes are fathomed.

Although a variety of strategies may be used for intelligently selecting branching variables and nodes to process, in the preferred embodiment, the branch-and-bound is coupled with other computational devices, such as problem preprocessing, primal heuristics, global and local reduced-cost fixing, and cutting planes.

In the preferred embodiment, global optimization module is based on a branch-and-bound MIP solver that is built on top of general-purpose mixed integer research code (MIP-SOL). The general purpose code, which incorporates all of the above mentioned computational devices, has been shown to be effective in solving a wide variety of large-scale real-world MIP instances.

System Implementation

Figure 3:
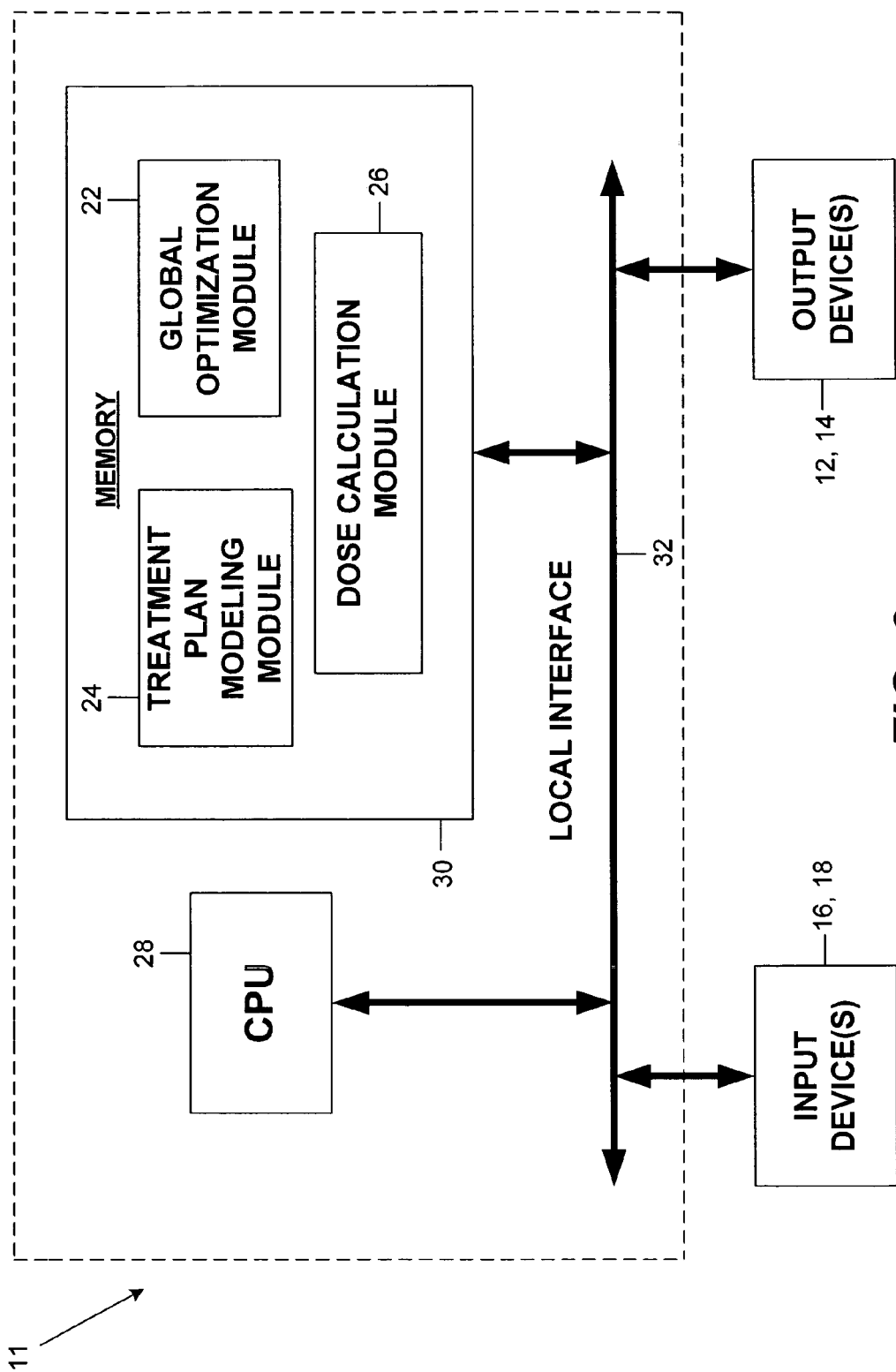
FIG. 3 is a block diagram of a preferred implementation of the system illustrated in FIG. 2.

System 10 of FIG. 1 and system 11 of FIG. 2 can be implemented in hardware, software, firmware, or a combination thereof. FIG. 3 illustrates a preferred implementation of system 11. As described above, system 11 is similar to system 10 except for the inclusion of dose calculation module 26. Thus, although the preferred implementation is described below, system 10 is implemented in a similar fashion.

As shown in FIG. 3, system 11 comprises computer processing unit (CPU) 28, memory 30, and local interface 32. System 11 may communicate via local interface 32 with input devices and output devices. As shown in FIG. 2, input devices may include three-dimensional imaging system 16 and/or input data 18 and output devices may include external beam delivery unit 12 and/or visual evaluation functionality 14.

Treatment plan modeling module 24, global optimization module 22, and dose calculation module 26 are implemented in software or firmware that is stored in memory 30 and executed by CPU 28. CPU 28 may be any suitable instruction execution system. It should be understood by persons skilled in the art that treatment plan modeling module 24, global optimization module 22, and dose calculation module 26 may also implemented in hardware. For example, in accordance with the systems and methods of the present invention, treatment plan modeling module 24, global optimization module 22, and dose calculation module 26 may be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 4:
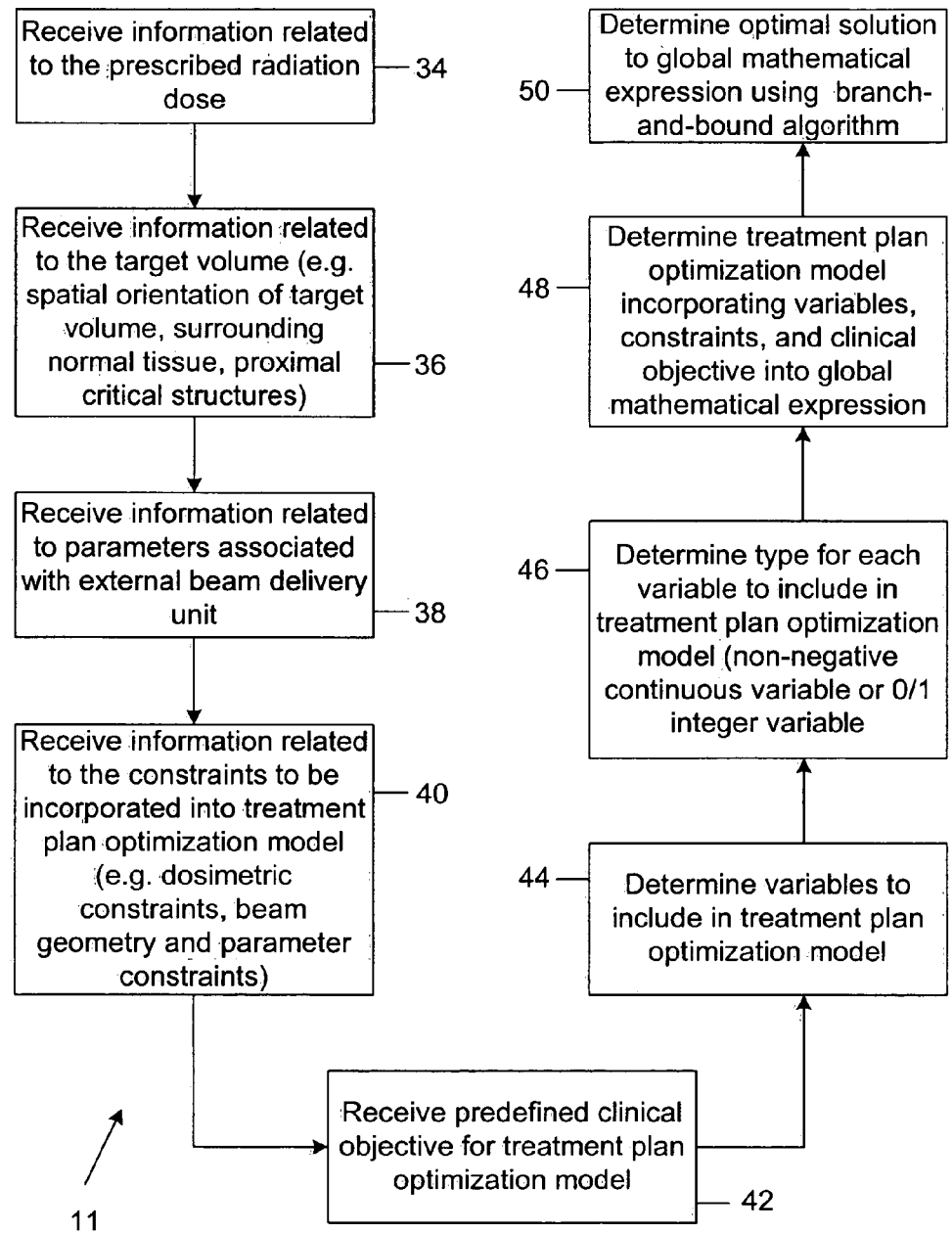
FIG. 4 is a flowchart illustrating the functionality and operation of the system illustrated in FIGS. 2 and 3.

The flowchart of FIG. 4 shows the functionality and operation of one implementation of system 11. Any process descriptions or blocks in flowcharts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

Referring to FIG. 4, at 34, information related to the prescribed dose is received. At 36, information related to target volume 20 is received. As described above, this information may include CT and/or MRI images identifying the contours of target volume 20 and surrounding normal tissue and critical structures. Information related to external beam delivery unit 12, such as beam geometry and beam parameters, is received at 38. At 40, information related to the constraints to be incorporated into the treatment plan optimization model is received. For example, the treatment plan optimization model may incorporate dosimetric constraints and constraints on various characteristics of the beam arrangements. At 42, predefined clinical objectives are received. At 44, the variables to include in the treatment plan optimization model are determined. As described above, the present invention employs a global approach, and thus, all possible variables are included in the treatment plan optimization model. At 46, the type of variable for each variable is determined, for example, whether the variable will be represented in the treatment plan optimization model as a non-negative continuous variable or a 0/1 integer variable. At 48, the treatment plan optimization model is determined by incorporating the variables, constraints, and the clinical objective into a global mathematical expression. At 50, a branch-and-bound algorithm is used to determine the optimal treatment plan.

Treatment plan modeling module 24, global optimization module 22, and dose calculation module 26, which comprise an ordered listing of executable instructions for implementing logical functions, can be embodied in any computer-readable medium for use by or in connection with CPU 28 or any other instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Intensity-Modulated Radiation Therapy (IMRT) Treatment Planning

As described above, systems 10 and 11 may employ any type of external beam delivery unit and/or radiation modality (e.g. static conformal radiation therapy (SCRT), non-coplanar arc stereotactic radiosurgery (NASR), intensity modulated radiation therapy (IMRT), intensity modulated arc therapy (IMAT), etc.). With reference to FIGS. 5–18, various exemplary embodiments of systems, methods, and computer programs will be described for implementing global optimization of IMRT treatment planning. These exemplary embodiments may include the components described above with respect to FIGS. 1–4 (e.g., global optimization module 22, treatment plan modeling module 24, dose calculation module 26, etc.), and may operate in a similar manner.

In IMRT, the beam intensity is varied across the treatment field. Rather than being treated with a single large, uniform beam, the patient is treated with many very small beams, each of which may be configured with a different intensity. Intensity modulation allows more intense treatment of the tumor, while limiting the radiation dose to adjacent healthy tissue. In the exemplary IMRT embodiments described below, the principles, operation, architecture, etc. of systems 10 and 11 (FIGS. 1–4) may be used by incorporating the appropriate data variables, user input, constraints (e.g., dosimetric, beam geometry, etc.), clinical objectives, etc. to determine the corresponding treatment plan optimization model(s) and optimization mathematics, as well as determine the globally optimal solutions for the IMRT treatment plan.

Figure 5:
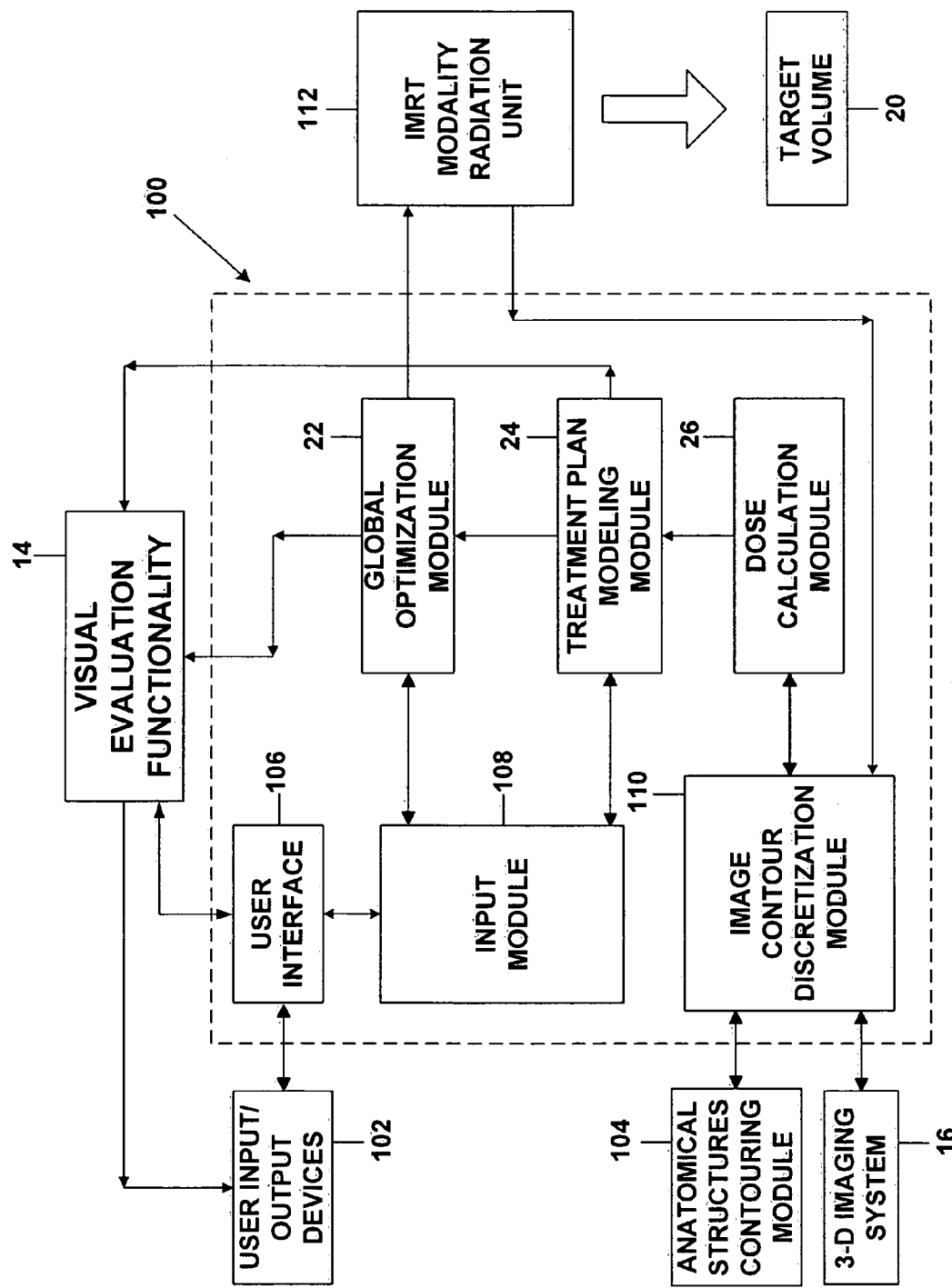
FIG. 5 is a functional block diagram of an embodiment of the systems of FIGS. 1–4, for intensity modulated radiation therapy (IMRT) treatment planning.

FIG. 5 illustrates a functional block diagram of one embodiment of an exemplary system 100 for providing global optimization of IMRT treatment planning. System 100 comprises global optimization module 22, treatment plan modeling module 24, dose calculation module 26, input module 108, user interface 106, and image contour discretization module 110. As further illustrated in FIG. 5, system 100 interfaces with various components, such as input/output (I/O) devices 102, anatomical structures contouring module 104, 3-D imaging system 16, IMRT modality radiation unit 112, and visual evaluation functionality 14.

In general, global optimization module 22, treatment plan modeling module 24, and dose calculation module 26 are configured to operate as described above. Nonetheless, these and other components will be described in more detail below. As an initial matter, however, the components of system 100 will be briefly described, as well as the interaction between these components. In this regard, it should be appreciated that user interface 106, input module 108, and image contour discretization module 110 generally provide functionality to enable global optimization module 22, treatment plan modeling module 24, and dose calculation module 26 to interface with I/O devices 102, anatomical structures contouring module 104, and 3-D imaging system 16. In other words, user interface 106, input module 108, and image contour discretization module 110 provide an appropriate environment for receiving various types of data (e.g., from a user or physician, other hardware component, software component, system, etc.) to be input to system 100. As described above, this and other data may be used to generate treatment plan optimization model(s) (treatment plan modeling module 24), define appropriate mathematics, variables, etc. for global optimization module 22, and/or perform a dose calculation (dose calculation module 26).

Referring again to FIG. 5, image contour discretization module 110 interfaces with dose calculation module 26, IMRT modality radiation unit 112, anatomical structures contouring module 104, and 3-D imaging system 16. In general, image contour discretization module 110 receives data related to the location of a target volume, surrounding critical structures, etc. from anatomical structures contouring module 104 and 3-D imaging system 16. Image contour discretization module 110 may also receive data input from IMRT modality radiation unit 112. As described in more detail below, the data received by image contour discretization module 110 may be processed and provided as input to dose calculation module 26. Furthermore, the output of the dose calculation module 26 is provided to treatment plan modeling module 24.

User interface 106 and input module 108 provide a suitable environment that enables a physician, system operator, etc. ("user") to provide various types of data to system 100 via I/O devices 102. For example, input module 108 interfaces with global optimization module 22 and treatment plan modeling module 24. In this regard, input module 108 may be configured to support interactive communication between the user and global optimization module 22 and treatment plan modeling module 24 (via user interface 106 and I/O devices 102). As described above and below in more detail, input module 108 may enable the user to input various types of criteria of interest for the treatment plan optimization model and the corresponding optimization mathematics (e.g., prescribed radiation dose, constraints, clinical objectives, variables to include in treatment plan optimization model, variable types, couch angles, field size, LAO gantry angle for each field, etc.).

System 100 may also comprise visual evaluation functionality 14. Visual evaluation functionality 14 enables the user to preview a particular IMRT treatment plan provided by treatment plan modeling module 24. Visual evaluation functionality 14 may also be used to enable the user to verify data that has been input to system 100 via input module 108, anatomical structures contouring module 104, 3-D imaging system 16, and IMRT modality unit 112. For example, if the data being previewed is incorrect, or simply undesirable, the user may edit the input data as desired. It should be appreciated that visual evaluation functionality 14 and I/O devices 102 may be integrated. In other words, visual evaluation functionality 14 may be integrated with user interface 106 to provide a visual display for the user.

As further illustrated in FIG. 5, treatment plan modeling module 24 also interfaces with global optimization module 22. The operation, architecture, and functionality of global optimization module 22, treatment plan modeling module 24, and dose calculation module 26 are generally described above. Furthermore, various exemplary IMRT embodiments of these modules are described below. However, in terms of the general operation of system 100, it should be appreciated that global optimization module 22 determines an optimal solution to the global mathematical expression defined by the treatment plan optimization model(s) generated by treatment plan modeling module 24. The optimal solution, which defines a globally optimal treatment plan, may be executed on target volume 20 by IMRT radiation modality unit 112.

Having generally described the components of system 100 and their interaction, various implementations of input module 108, image contour discretization module 110, global optimization module 22, treatment plan modeling module 24, and dose calculation module 26 will be described relative to FIGS. 6–18.

Figure 6:
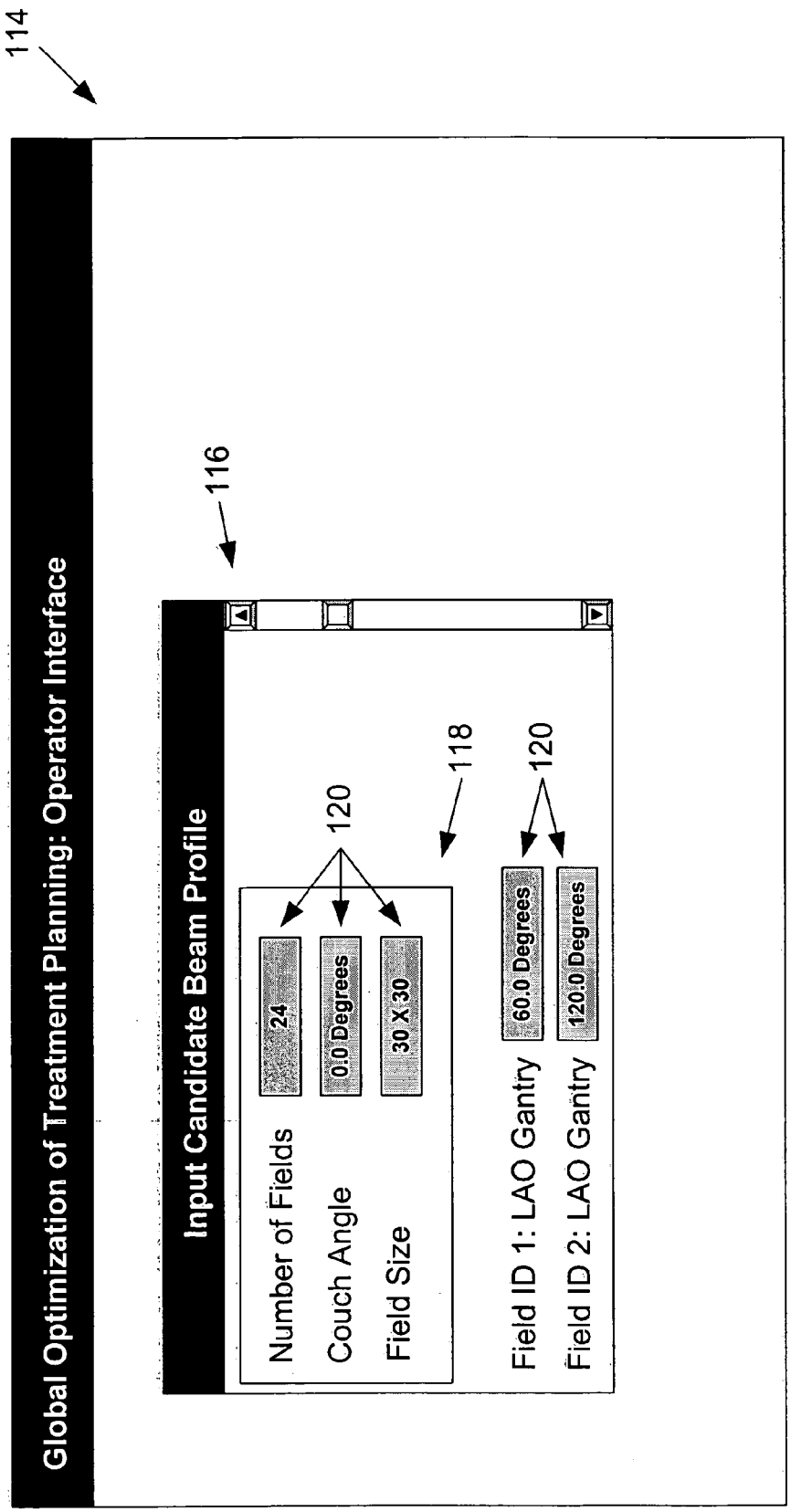
FIG. 6 is a screenshot of an embodiment of a user input screen supported by the user interface of FIG. 5 for enabling a user to designate values for a candidate beam profile for IMRT treatment planning.

As mentioned above, a user may interface with system 100 via various types of I/O devices 102 in communication with user interface 106, input module 108, etc. At various stages in the development of the treatment plan optimization model(s) and the optimal treatment plan, system 100 may require input from the user. In this regard, user interface 106 may be configured in a number of ways. For instance, FIG. 6 is a screen shot illustrating one of a number of embodiments of a user interface 106 configured to enable the user to provide input to system 100 via input module 108. The embodiment of FIG. 6 supports a graphical user interface (GUI) environment. It should be appreciated that alternative designs may be employed, such as a command-based interface and others.

FIG. 6 is an example of a user input screen 114 supported by a graphical user interface for enabling a user to input various types of input data. In the embodiment illustrated in FIG. 7, user interface 106 provides a window 116 in which a user may input, for example, the number of fields (beams), the couch angle, the dimensions of each field in terms of an array of beamlets (e.g., 30×30), and the LAO gantry angle for each field to be used for the IMRT treatment plan. This data and other types of data may be used to develop the treatment plan optimization module, which is used by global optimization module 22 to develop a globally optimal IMRT treatment plan.

FIG. 7 is another embodiment of a user input screen 122 supported by user interface 106, which enables a physician to input various additional types of data to system 100. As illustrated in FIG. 7, user input screen 122 may comprise a window 124 in which the physician may specify various data related to the anatomical structures associated with target volume 20. In the embodiment of FIG. 7, the physician has specified various regions within the target volume 20 (e.g., a "tumor" region, a "critical structures" region, and a "normal tissue" region). User input screen 122 enables the physician to specify the corresponding anatomical structures for each of these regions (i.e., prostate, rectum and bladder, and skin). As illustrated in FIG. 7, user interface 106 may provide text boxes (shaded boxes in FIG. 7) for inputting the data. User input screen 122 further enables the physician to select the structures and specify the prescription dose, and the lower and upper bound factors for the corresponding anatomical structures. The physician may also specify the following, and other, types of information: tumor coverage, homogeneity, number of input candidate beams, and number of output beams. Any of these, and other, types of data may be used to develop the treatment plan optimization model(s). As known in the art, prescription dose refers to the radiation dose the clinician prescribed to the tumor target. Lower and upper bound factors correspond to the fraction of prescribed dose that can be tolerated by various anatomical structures. These dose limits are represented with respect to the prescribed dose. Coverage refers to the percentage of tumor volume receiving the prescribed dose, and homogeneity indicates the ratio of the maximum dose to the tumor to the minimum dose to the tumor.

FIG. 8 illustrates a further embodiment of a user input screen 126 supported by user interface 106, which enables a physician to input various types of data related to the radiation doses for the anatomical structures specified in FIG. 7. In the embodiment illustrated in FIG. 8, user input screen 126 enables the physician to specify data related to prescription data, dose volume constraints, clinical objectives, and physical constraints. For a given structure, the dose-volume histogram (DVH) is a graph which plots as a function of dose, D, the probability that a randomly-selected voxel volume receives a dose of at least D. This information can be incorporated within the treatment planning optimization using the dose volume constraints. Many clinical objectives (e.g., maximizing mean dose to target, minimizing radiation to critical structures, etc.) can be input in this module by the clinician, or the user. The physical constraints describe the number of beams and physical parameters the user would prefer in the resulting treatment plan.

It should be appreciated that system 100 may receive a variety of alternative data inputs via user input screens supported by user interface 106. As described above in detail, systems 10, 11, and 100 may use any of the following, or other, types of information as input to dose calculation module 26, treatment plan optimization module 24, and global optimization module 22: information related to the prescribed radiation dose; information related to the target volume (e.g., spatial orientation of target volume, surrounding normal tissue, proximal critical structures, etc.); information related to external beam delivery unit 12 (e.g., # of beams, couch angle, field size, etc.); information related to constraints to be incorporated into the treatment plan optimization model (e.g., dosimetric constraints, beam geometry and parameter constraints, etc.); clinical objectives; other variables to include in treatment plan optimization model; and type of variable (e.g., non-negative continuous, 0/1 integer, etc.). This data may also be used to develop the treatment plan optimization model(s) or to configure the dose calculation module or global optimization module 22.

Figure 9:
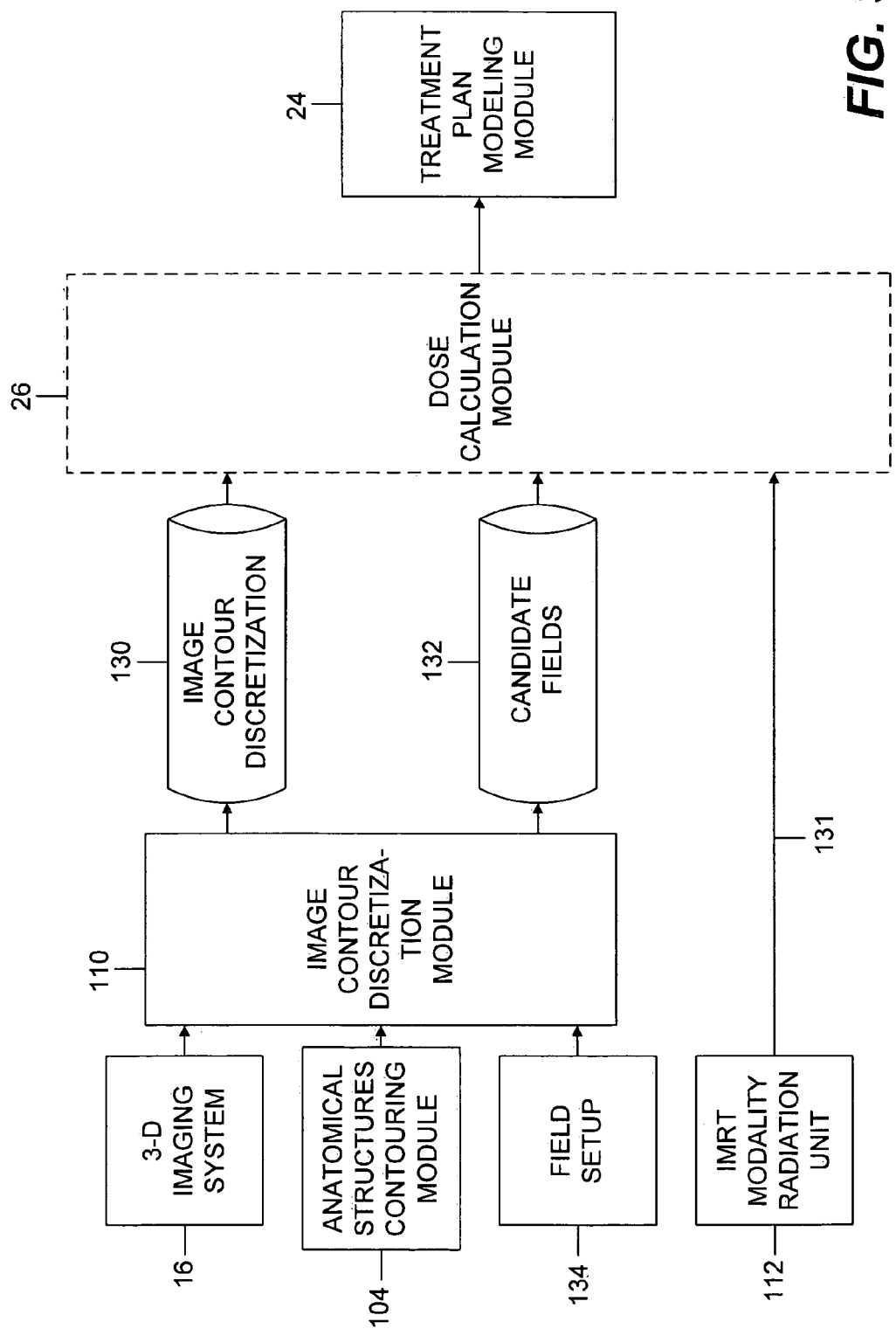
FIG. 9 is a diagram illustrating the functional connectivity and data flow for an embodiment of the dose calculation module of FIG. 5 for IMRT treatment planning.

Referring to FIGS. 9–18, the architecture, operation, and/or functionality of various embodiments of dose calculation module 26, treatment plan optimization module 24, and global optimization module 22 will be described. FIG. 9 is a flow chart illustrating various data inputs to an embodiment of dose calculation module 26 for IMRT treatment planning. In the embodiment illustrated in FIG. 9, dose calculation module 26 interfaces with image contour discretization module 110, treatment plan modeling module 24, and IMRT modality radiation unit. As described above with respect to FIGS. 5–8, image contour discretization module 110 may receive various types of information from 3-D image system 16, anatomical structures contouring module 104, and a field setup module 134. For example, image contour discretization module 110 may receive any of the following, or other, types of data: CT/MR scans with tumor and critical structures outlined by the clinician; number, direction and angle of beams in the IMRT modality radiation unit 112, etc. In certain embodiments, image contour discretization module 110 may superimpose image registration data from the 3-D image system 16 and anatomical structures contouring module 104 and provide image contour discretization data 130 and candidate fields data 132 to dose calculation module 26. As known in the art, various types of data from radiation unit 112 may also be provided to dose calculation module 26 via interface 131. As described above in detail, dose calculation module 26 may use standard dose calculation tools to calculate, for each voxel, the dose contribution per monitor unit of radiation from each beamlet in each field.

Figure 10:
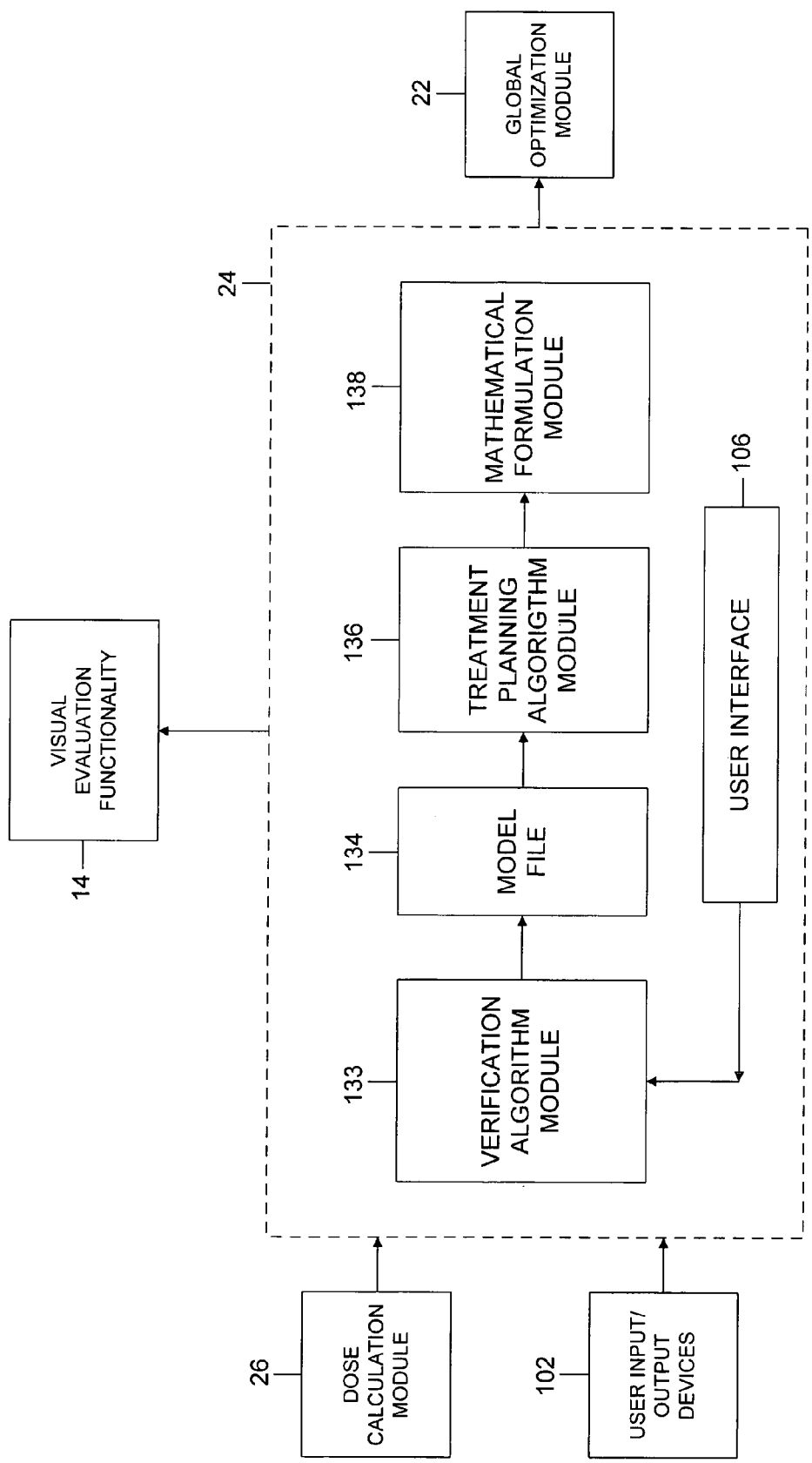
FIG. 10 is a functional block diagram illustrating the architecture, operation, and/or functionality of an embodiment of the treatment plan modeling module of FIG. 5 for IMRT treatment planning.

FIG. 10 is a flow chart illustrating the general architecture, operation, and/or functionality of an embodiment of treatment plan modeling module 24. In the embodiment of FIG. 10, treatment plan modeling module 24 comprises a verification algorithm module 133, a model file 134, a treatment planning algorithm module 136, and a mathematical formulation module 138. As illustrated in FIG. 10, all relevant input data from dose calculation module 26 and I/O devices 102 is provided to verification algorithm module 133. The architecture, operation, and functionality of an embodiment of verification algorithm 133 is described below in detail with reference to FIG. 11. Verification algorithm module 133 outputs data to a model file 134. Model file 134 contains all of the data to be used to define the global mathematical expression for the treatment plan optimization model. The user may view data from model file 134 on visual evaluation functionality 14. Data from model file 134 is input into a treatment planning algorithm module 136. The architecture, operation, and functionality of an embodiment of treatment planning algorithm module 136 is described below in detail with reference to FIG. 12. Treatment planning algorithm module 136 sends data to mathematical formulation module 138 to determine the global mathematical expression to be optimized by global optimization module 22. At various points in this process, treatment modeling module 24 may provide outputs to visual evaluation functionality 14, from which the user may verify and either accept or modify through I/O devices 102. After a treatment plan optimization model is generated, the global mathematical expression is provided to global optimization module 22.

Figure 11:
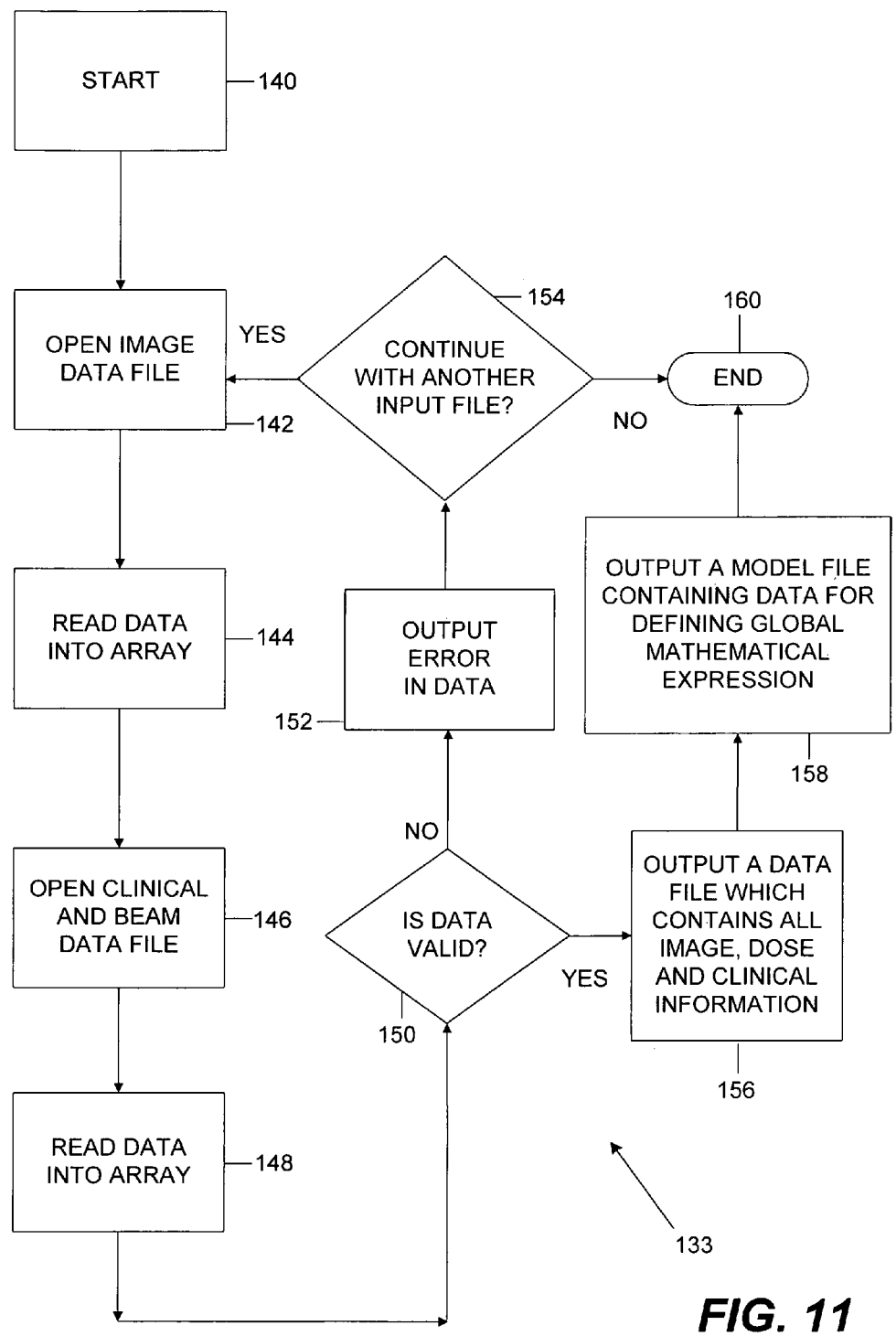
FIG. 11 is a flow chart illustrating the architecture, operation, and/or functionality of an embodiment of the verification algorithm module of FIG. 10 for IMRT treatment planning.

FIG. 11 is a flow chart illustrating the architecture, operation, and functionality of an embodiment of verification algorithm module 133. After beginning at block 140, verification algorithm module 133 may open an image data file from dose calculation module 26 at block 142. The image data comprises the structures that will be used for modeling the treatment plans, the number of voxels discretized for each structure, the number of candidate beams generated, and the associated dose contribution per monitor unit to each voxel (of each structure) from each beamlet generated from the set of all candidate beams. Verification algorithm module 133 will check that this data is consistent and the dose for each voxel and each beamlet is registered in the file, and compile all this data into a single file for modeling purposes. At block 144, verification algorithm module 133 may process the data into an array. At block 146, verification algorithm module 133 opens a clinical and beam data file containing information regarding clinical properties, beam properties, etc. The clinical beam and data file(s) contain the prescription dose, dose bounds, dose volume restrictions for each structure, clinical metrics (e.g. coverage, conformity, homogeneity) for the target volume, and physical beam profile for input and output purposes (e.g. the total number of candidate beams used for setting up the treatment models, and the desired number of output beams for treating the patients). At block 148, verification algorithm module 133 may process this data into another array. At decision block 150, verification algorithm module 133 performs a validity check to determine whether the data in the arrays is valid. If the data is not valid, at block 152, an output error is provided to the user and the user may proceed with another file, edit the file, etc. (block 154). The validity check may be configured to determine, for example, whether the number of beams (fields) is consistent in all files, whether there are missing dose values for any voxel, whether the prescription dose is given, whether the dose level is consistent and feasible, whether all the input for the anatomical structures is accounted for, and whether the biological and clinical factors are well defined, to name a few.

If the data is valid, at block 156, verification algorithm module 133 outputs a data file which contains all image, dose, and clinical information. At block 158 verification algorithm module 132 outputs model file 134. Verification algorithm module 132 terminates at block 160.

Figure 12:
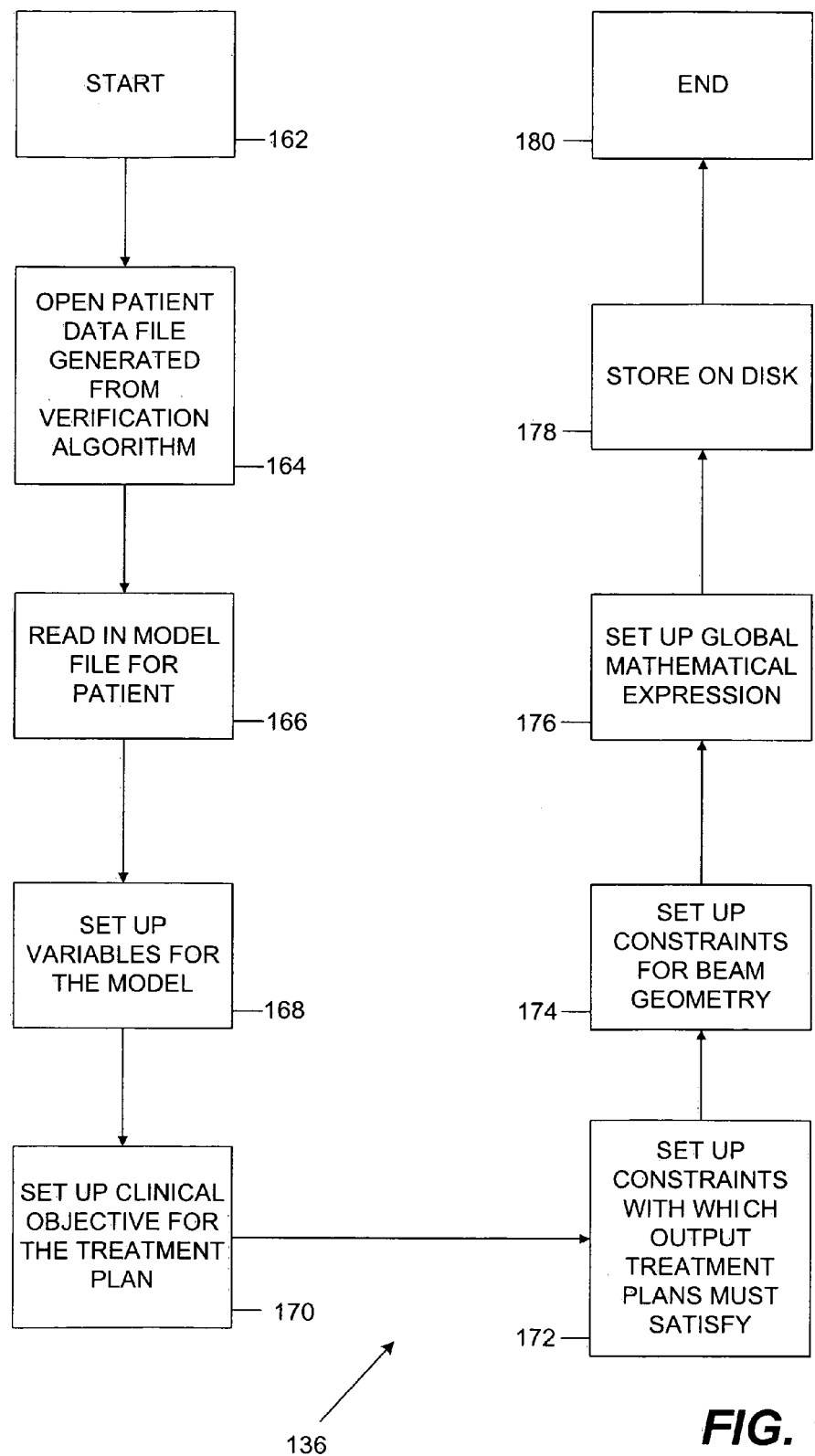
FIG. 12 is a flow chart illustrating the architecture, operation and/or functionality of an embodiment of the treatment planning algorithm module of FIG. 10 for IMRT treatment planning.

FIG. 12 is a flow chart illustrating the architecture, operation, and/or functionality of an embodiment of treatment planning algorithm module 136. After beginning at block 162, at block 164, treatment planning algorithm module 136 opens a patient data file. The patient data file corresponds to the data file output 158 (FIG. 11) by verification algorithm module 133. In general, it comprises all image voxels and dose and clinical information for modeling purposes. At block 166, treatment planning algorithm module 136 reads in model file 134 used for the patient. At block 168, treatment planning algorithm module 136 sets up variables for the treatment plan optimization model. At block 170, treatment planning algorithm module 136 sets up a clinical objective for the treatment plan. It should be appreciated that the objective may be defined according to the clinical setting, patient, treatment, etc. For example, the clinical objective may include maximizing mean tumor dose, minimizing total dose to critical structures, maximizing dose falloff outside tumor volume, etc. It should be further appreciated that the clinical objective may be extracted from model file 134. The clinical objective may be used to drive the search process (for an optimal treatment plan) in the optimization process. At block 172, treatment planning algorithm module 136 sets up the specified constraints (e.g., physical constraints, dose constraints, etc.) for the treatment plan optimization model. At block 174, treatment planning algorithm module 136 sets up the specified constraints for beam geometry. At block 178, treatment planning algorithm module 136 defines a global mathematical expression based on model file 134, relevant variables, the specified clinical objective(s) and constraint(s), etc. This global mathematical expression defines the treatment plan optimization model. It should be appreciated that other variables may be incorporated in the model as desired for IMRT treatment planning. At block 178, treatment planning algorithm module 136 may store the treatment plan optimization model, and, at block 180, treatment planning algorithm module 136 ends.

Figure 13:
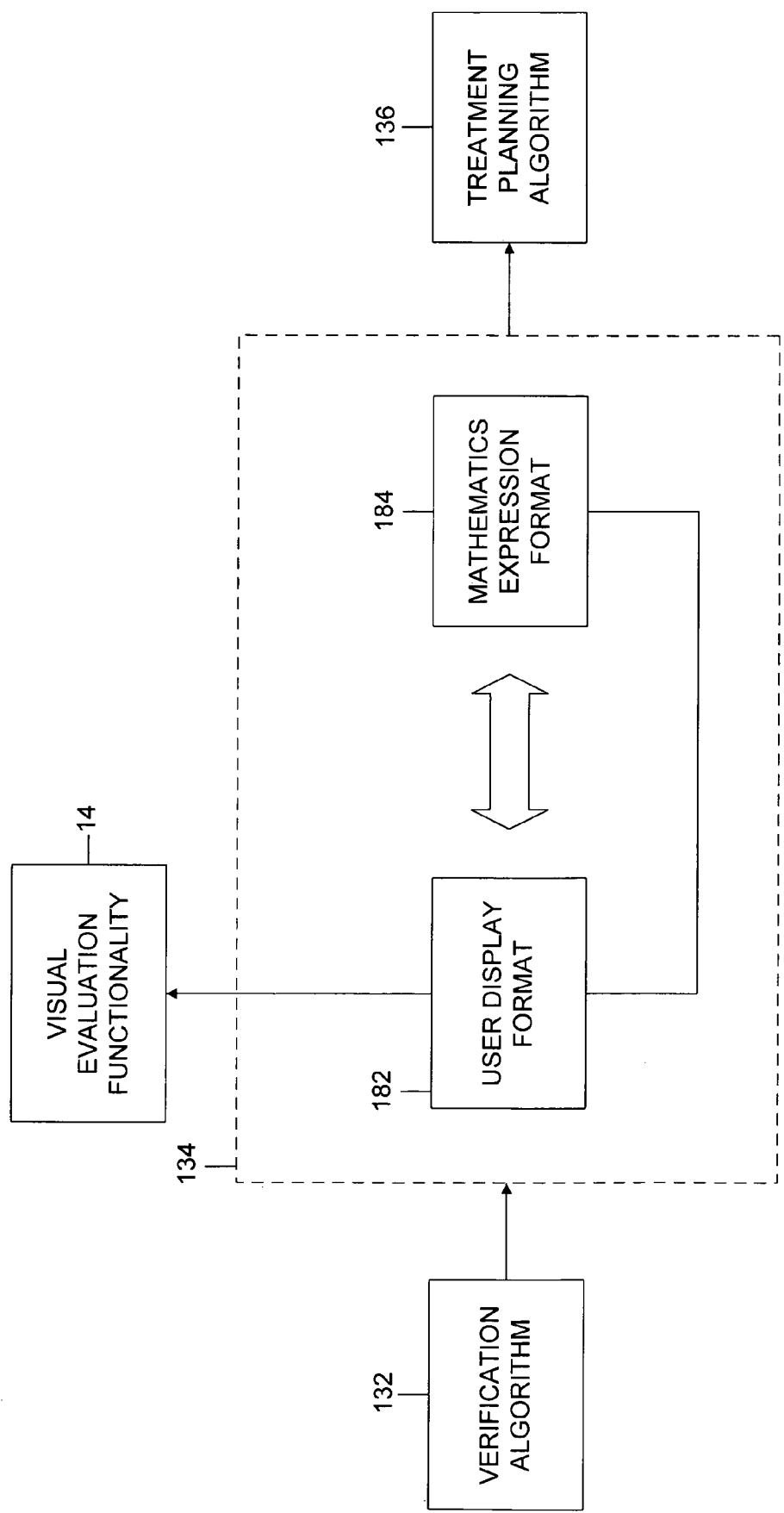
FIG. 13 is a block diagram illustrating an embodiment of the model file of FIG. 10 for IMRT treatment planning.

FIG. 13 is a functional block diagram illustrating an embodiment of model file 134. As described above with regard to FIG. 10, verification algorithm module 133 may output model file 134 to a user. Referring to FIG. 13, model file 134 may comprise two formats. For example, model file 134 may be presented in a format suitable for display to the user via visual evaluation functionality 14 (user display format 182). Model file 134 may also comprise a format suitable for mathematical expression (format 184). The reason for these two formats is that the user generally lacks the technical expertise to comprehend model file 134 in the mathematics expression format 184. Furthermore, mathematics expression format 184 may contain data not relevant to the user's needs. System 100, therefore, may output data in a form most beneficial to the user. Model file 134 is provided to treatment planning algorithm 136.

Figure 14:
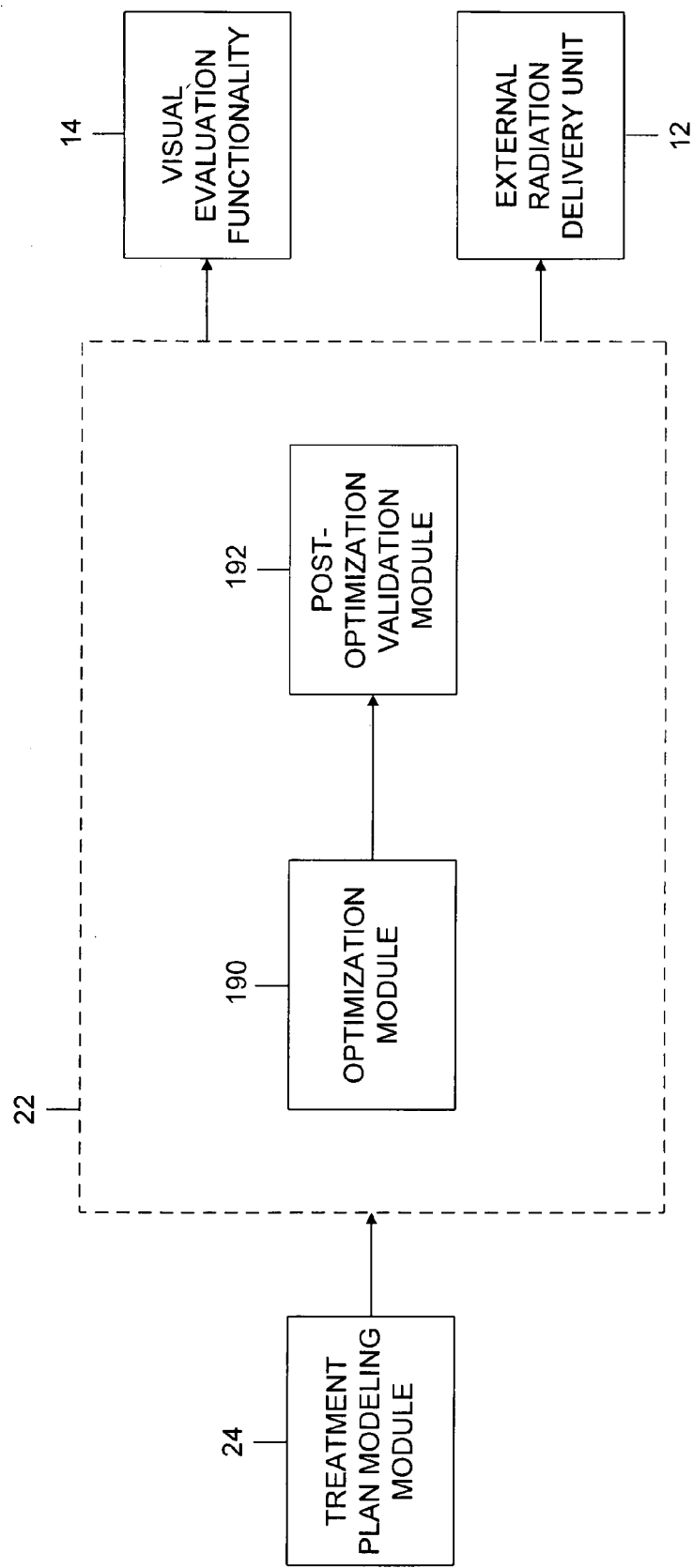
FIG. 14 is a functional block diagram illustrating the architecture, operation and/or functionality of an embodiment of the global optimization module of FIG. 5 for IMRT treatment planning.

FIG. 14 is a functional block diagram illustrating the architecture, operation, and/or functionality of an embodiment of global optimization module 22 for IMRT treatment planning. As described above, treatment plan modeling module 24 outputs the treatment plan optimization model(s) to global optimization module 22. The embodiment of global optimization module 22 illustrated in FIG. 14 comprises includes two components: optimization module 190 and post-optimization validation module 192. Optimization module 190 determines the most optimal solution within the solution space for the treatment plan optimization model, and sends the output solution to post-optimization validation module 192. Post-optimization validation module 192 calculates various forms of statistical data related to the optimal treatment plan, and sends that data to visual evaluation functionality 14.

Figure 15:
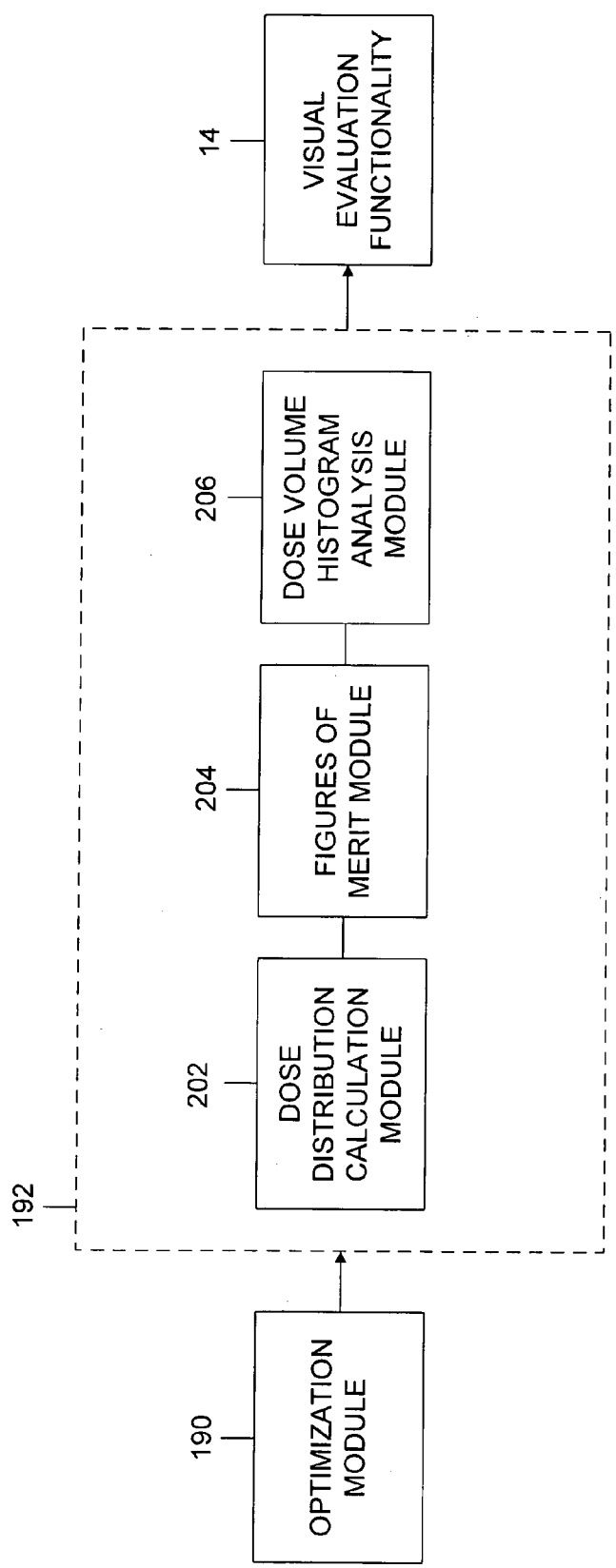
FIG. 15 is a functional block diagram illustrating the architecture, operation and/or functionality of an embodiment of the optimization module of FIG. 14 for IMRT treatment planning.

FIG. 15 illustrates the architecture, operation, and/or functionality of an embodiment of post-optimization validation module 192. As illustrated in FIG. 15, optimization module 190 outputs the globally optimal treatment plan into post-optimization validation module 192. The internal components of post-optimization module 192 may comprise, for example, dose distribution calculation module 202, clinical metrics module 204, and dose volume histogram analysis module 206. Dose distribution calculation module 202 calculates the dose to be distributed to various parts (e.g., anatomical structures) of the patient related to the globally optimal plan. Clinical metrics module 204 may be configured to provide various visual tools (e.g., coverage, homogeneity, conformity, $D_{95}$, the dose level which covers 95% of tumor target, $V_{20}$, the volume receiving more than 20 Gy, etc.) related to the globally optimal treatment plan. As the name suggests, dose volume histogram analysis module 186 may generate and display a dose volume histogram for the globally optimal treatment plan and display it on visual evaluation functionality 14.

Figure 16:
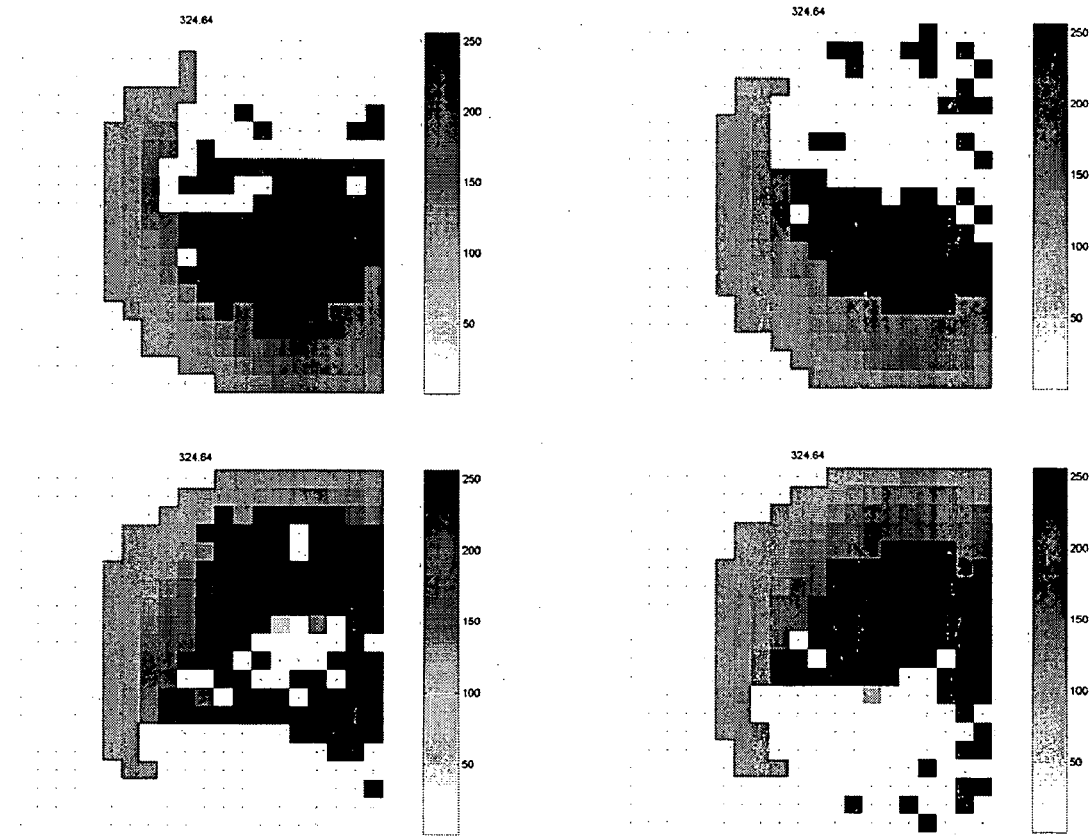
FIG. 16 is a screenshot of an embodiment of a beam intensity tool supported by the system of FIG. 5.

It should be appreciated that global optimization module 22 may include any type of module(s) for enabling the user to view, assess, etc. the globally optimal treatment plan generated by optimization module 190. For example, FIG. 16 is a screenshot illustrating one embodiment of a visual tool—an intensity map of target volume 20. As a non-limiting example, FIG. 16 illustrates the various beamlet intensities of four different fields of IMRT radiation modality unit 112. In this particular example, each field includes a 20×20 array of beamlets. FIG. 16 further illustrates that each field has different beamlet intensities, and that no field is dependent on any other field. The scale to the right of each intensity diagram in FIG. 16 illustrates that the dark shading represents higher intensity, while the lighter shading represents lower intensity. As stated above with respect to FIG. 6, each field has a gantry angle and a diversity of beamlet intensities converging at, or around, target volume 20, which may result in various shapes of treatment dose to better conform to target volume 20.

Figure 17:
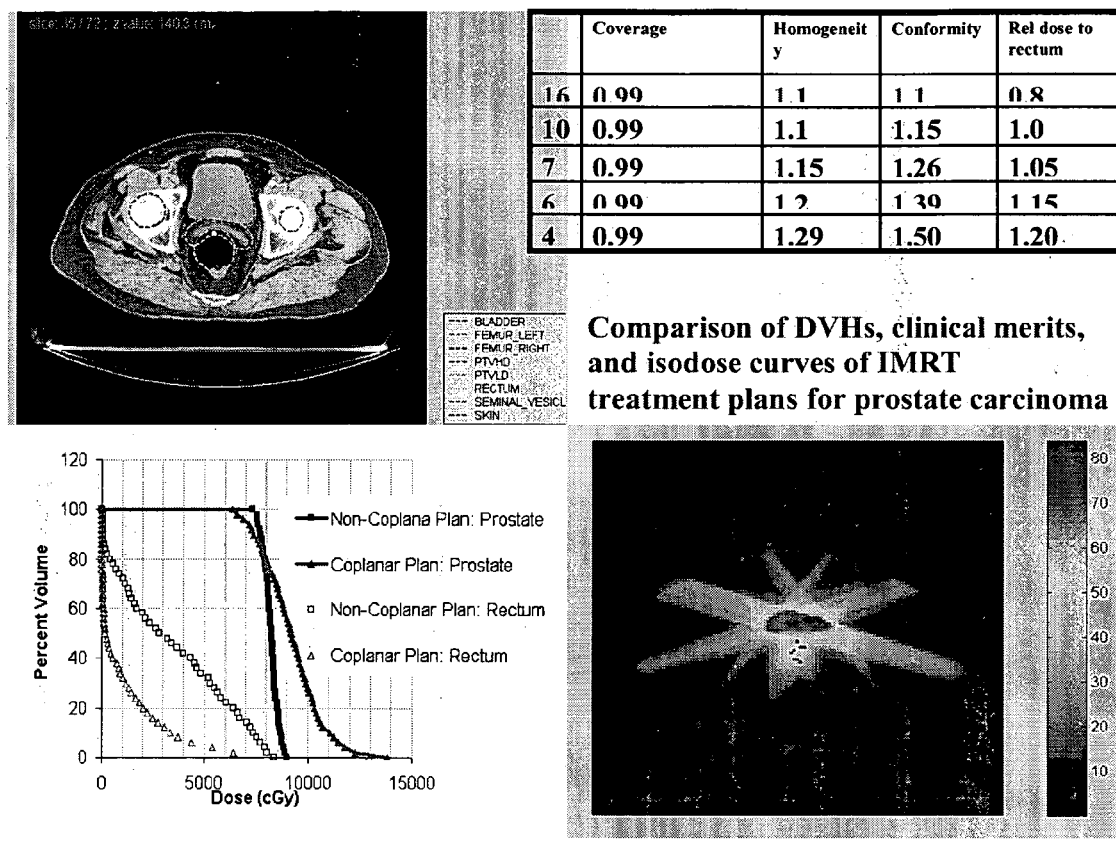
FIG. 17 illustrates the beam intensity data of FIG. 16 in numerical and tabular form.

While FIG. 16 illustrates beamlet intensities graphically, FIG. 17 illustrates the values numerically. FIG. 17 is an example of another visual tool for displaying beamlet intensities of IMRT radiation modality unit 112. This particular embodiment illustrates a field with 400 beamlets, which is organized in a 20×20 configuration. As shown in FIG. 17, the intensities of each beamlet can vary substantially, and are not constrained by other beamlets in the array.

Figure 18:
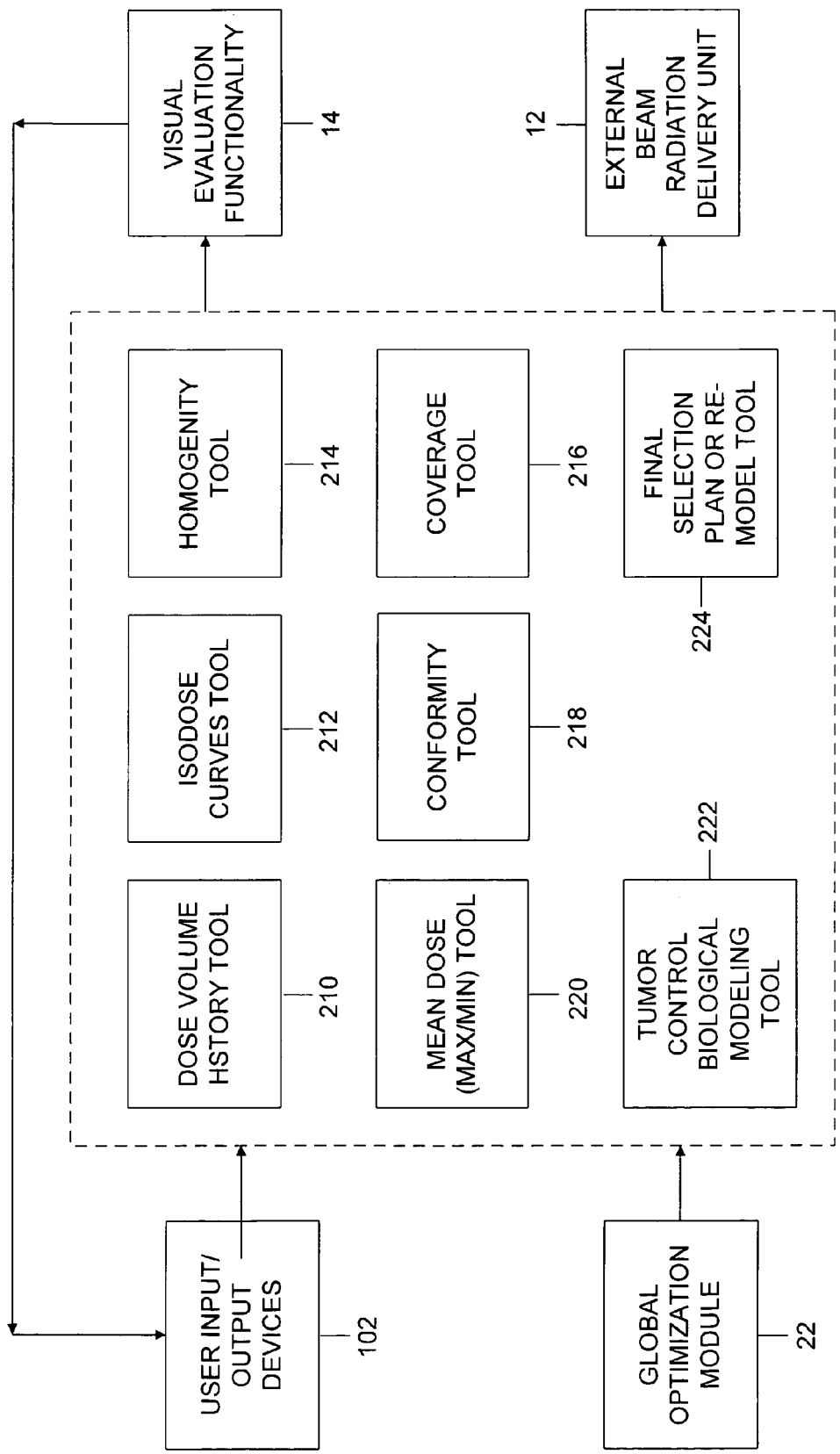
FIG. 18 is a block diagram illustrating various alternative tools supported by the system of FIG. 5 for enabling a user to evaluate the IMRT treatment plan.

As mentioned above, in developing and reviewing the globally optimal treatment plan, various data may be pertinent to the user. This data may be displayed on visual evaluation functionality 14. In this regard, FIG. 18 is a block diagram illustrating various other visual tools, resources, etc. that may be provided to the user. As shown in FIG. 18, these tools may be integrated with visual evaluation functionality 14 to enable the user to view various aspects of the globally optimal treatment plan before it is implemented on the patient. For example, system 100 may support any of the following, or other, types of tools: dose volume history tool 210, isodose curves tool 212, homogeneity tool 214, mean dose (max/min) tool 220, conformity tool 218, coverage tool 216, tumor control biological modeling tool 222, and final selection plan or re-model 224. The isodose curves tool 212 describes the contour of dose level for each structure. The homogeneity, coverage and conformity tools 214, 216, and 218 describe the dose distribution, tumor coverage and tightness of prescription isodose curves to the tumor volume. The tumor control biological modeling tool 222 calculates the tumor control probability and normal tissue complication probability values associated with the globally optimal treatment plan. The mean dose (max/min) tool 220 provides dose distribution statistics for the tumor and other anatomical structures associated with the globally optimal treatment plan. If the user determines this is data reflects a suitable treatment plan, the user may send a command to initiate the globally optimal treatment plan (i.e., implement the treatment plan on the patient). If the user determines that the data displayed on the visual evaluation functionality does not reflect a suitable treatment plan, the user may edit the treatment plan as desired or configure a new treatment plan optimization model, enter new data, and determine new globally optimal treatment plan.

With FIGS. 5–18 and the corresponding text as a backdrop, a further embodiment of a treatment plan optimization model and global optimization module 22 will be described, which incorporates a mixed integer programming approach.

As detailed above, for intensity-modulated radiation therapy (IMRT), the shape of the beams, and the combinations of open and closed MLC leaves control and modulate the intensity. This may provide the ability to dynamically vary the dose to accommodate the shape of the tumor from different angles so as to deliver full tumoricidal dose, while normal tissue is spared from excess radiation.

In the IMRT optimization schemes employed in systems 10, 11, and 100, photon fluence from a beam may be subdivided into "beamlets," which may be imagined to be divergent rectangular solids of fluence emanating from a radiation source in the treatment head of the linear accelerator (LINAC). One dimension of these beamlets, call it the "height," is defined by the projection of the MLC leaves onto a plane that is perpendicular to the central axis of the LINAC's beam and located at the rotational isocenter of the LINAC. These height projections may be between 0.5 and 1.0 cm. In the "width" direction the resolution of the beamlet (projected on the same plane) may be between 0.2 and 1.0 cm.

In treatment plan modeling module 24 and global optimization module 22, optimization may be performed over beamlets, rather than "beam segments" or "field segments," which are collections of beamlets that have been set to have the same intensity. The use of field segments may be advantageous for two reasons: (1) aggregations of many very small field dose calculations (i.e., on the order of a single beamlet) may be difficult; and (2) treatment time is proportional to the number of fields delivered. For reasons of economy and patient comfort, treatment times may be kept short.

Radiation dose, measured in Gray (Gy), is energy (Joules) deposited locally per unit mass (Kg). Fluence for external beam photon radiation may be defined mathematically by the number of photon crossings per surface area. Dose tends to be proportional to fluence, but is influenced by photon and electron scatter in the patient's tissues as well as the energy and media involved. For any beam, selection of beamlet fluence weights results in a "fluence map" (intensity map) for that beam.

As described below, global optimization module 22 and treatment plan modeling module 24 may be configured to optimize each of the following beam delivery parameters:

beamlet fluence weights, most current optimization algorithms for IMRT treatment planning search the space of beamlet fluence weights only. By way of additional background, the planning process begins when the patient is diagnosed with a tumor mass and radiation is selected as part of the treatment regime. A 3D image, or volumetric studyset, of the affected region, which contains the tumor mass and the surrounding areas, is acquired via 3D imaging system 16 (e.g., computed tomography (CT) scans). This CT data is used for treatment planning, and electron density information derived from it is used in the photon dose calculations for the beamlets. Additionally, magnetic resonance imaging (MRI) scans may be acquired, fused with the CR volumetric studyset, and used to identify the location and extents of some tumors—especially those in the brain. Based on these scans, the physician outlines the tumor and anatomic structures that need to be held to a low dose during treatment.

Typically, several regions of the tissue to be treated are identified. The gross target volume (GTV) represents the volume which encompasses the known macroscopic disease; that is, the disease that can be seen by the oncologist. The clinical target volume (CTV) expands the GTV to include regions of suspected microscopic disease. The planning target volume (PTV) includes additional margins for anatomical and patient setup uncertainties; that is, how the patient's organs and the patient will move from day to day. All volumetric data is discretized into voxels (volume elements) at a granularity that is conducive both to generating a realistic treatment plan optimization model and to ensuring that the resulting treatment planning integer programming instances are tractable (i.e., capable of being solved in a reasonable amount of computational time).

Dose calculation module 26 may involve the principle of convolving the total energy release in the patient from the radiation source with Monte Carlo-generated energy disposition kernels and superposition of pencil beam (SPPB) using fundamental physics describing photon and electron interactions and transport. Dose calculation module 26 may account for the transport of primary and secondary radiation inside the patient, the variation of beam intensity across the patient surface, the effects of tissue inhomogeneities on the dose, and the irregular blocked or multi-leaf (MLC) shaped fields. Dose calculation module 26 may comprise the following three components for computing the 3D dose distribution:

- Modeling the incident energy fluence as it exits the head of the linear accelerator.
- Projection of this incident fluence through the density representation of a patient to compute a Total Energy Released per unit MAss (TERMA) volume.
- A three-dimensional superposition of the TERMA with an energy deposition kernel using a ray-tracing technique to incorporate the effects of heterogeneities on lateral scatter.

Dose calculation module 26 may compute the dose to points, D(r). The dose at point D(r) comprises contributions from the shower of secondary particles resulting from primary interactions at radii r'. The SPPB model provides accurate results within areas of electronic disequilibrium and tissue heterogeneities.

For each beamlet, the dose per intensity to a voxel is calculated using this dose engine. The total dose per intensity deposited to a voxel is equal to the sum of dose deposited from each beamlet. For each patient, 16 non-coplanar candidate fields are generated. The size of the candidate fields and the associated number of beamlets is patient and tumor size dependent; varying from 10×10 cm$^2$ with 400 beamlets per field to 15×15 cm$^2$ with 900 beamlets per field. This results in a large set of candidate beamlets used for instantiating the treatment plan optimization model.

Treatment plan modeling module 24 and global optimization module 22 may employ the following mixed integer programming approach. Let B denote the set of candidate means, and let $N_i$ denote the set of beamlets associated with beam i∈B. Beamlets associated with a beam can only be used when the beam is chosen to be "on." If a beam is on, the beamlets with positive dose intensity will contribute a certain amount of radiation dosage to each voxel in the target volume and other anatomical structures. Once the set of potential beamlet intensities is specified, the total radiation dose received at each voxel can be modeled. Let $w_{ij} \geq 0$ denote the intensity of beamlet j from beam i. Then the total radiation dose at a voxel P is given by the following expression:

$$\sum_{i \in B} \sum_{i \in N_i} D_{P,ij} w_{ij}. \qquad \text{Equation 8}$$

where $D_{P,ij}$ denotes the dose per intensity contribution to voxel P from beamlet j in beam i. Various dose constraints are involved in the design of treatment plans. Clinically prescribed lower and upper bounds, say $L_P$ and $U_P$, for dose at voxel P are incorporated with Equation 8 to form the basic dosimetric constraints:

$$\sum_{i \in B} \sum_{j \in N_i} D_{P,ij} w_{ij} \geq L_P \text{ and } \sum_{i \in B} \sum_{i \in N_i} D_{P,ij} w_{ij} \leq U_P \qquad \text{Equation 9}$$

Aside from constraining the dose received by each voxel within anatomic structures, treatment plan modeling module 24 may constrain the number of beams used in the final beam profile. The motivation for this is that a simple plan (with a relatively small number of beams) may be preferred by a physician over a more complex plan, since a complex plan takes more time to implement in the delivery room and offers more chances for errors. Let $x_i$ be a binary variable denoting the use or non-use of beam i. The following constraints limit the total number of beams used in the final plan and ensure that beamlet intensities are zero for beams not chosen:

$$w_{ij} \leq M_i x_i \text{ and } \sum_{i \in B} x_i \leq B_{\max} \qquad \text{Equation 10}$$

Here, $M_i$ is a positive constant which can be chosen as the largest possible intensity emitted from beam I, and $B_{max}$ is the maximum number of beams desired in an optimal plan.

Dose-volume relationships within different anatomical structures are set up based on these constraints. Clinically, it is typically acceptable when 95% of the PTV receives the prescription dose, PrDose. The coverage constraints for PTV can be modeled as:

$$\sum_{i \in \beta} \sum_{i \in N_i} D_{P,ij} w_{ij} - r_P = PrDose, P \in PTV \quad \text{Equation 11}$$

$$r_P \leq D_{PTV}^{OD} v_P \quad \text{Equation 12}$$

$$r_P \geq D_{PTV}^{UD}(v_P - 1) \quad \text{Equation 13}$$

$$\sum_{P \in PTV} v_P \geq \alpha |PTV| \quad \text{Equation 14}$$

Here, $v_P$ is a 0/1 variable which captures whether voxel P satisfies the prescription dose bounds or not; $r_P$ is a real-valued variable that measures the discrepancy between prescription dose and actual dose; α corresponds to the minimum percentage of coverage required (e.g., α=0.95); $D_{PTV}^{OD}$ and $D_{PTV}^{UD}$ are the maximum overdose and maximum underdose levels tolerated for tumor cells; and |PTV| represents the total number of voxels used to represent the planning target volume. The values $D_{PTV}^{OD}$ and $D_{PTV}^{UD}$ may be chosen with care to provide a feasible system of constraints.

It may be desirable that dose received by organs/tissues other than the tumor volume be minimal, as there is a direct correlation between the level or radiation exposure and normal tissue toxicity. Thus, for other anatomical structures involved in the planning process, along with the basic dose constraints given in Equation 9 additional binary variables are employed for modeling the dose-volume relationship. The dose-volume relationship is a standard metric that clinicians use when assessing a plan. It is a quantitative measure of the percentage volume of the anatomical structure receiving dose within specified intervals. To incorporate this concept into the model, let $\alpha_k, \beta_k \in (0,1)$ for k in some index set K, and let $y_P^{\alpha_k}$ and $z_P^{\alpha_k}$ be binary variables. Then the following set of constraints ensures that at least $100\beta_k\%$ of the voxels in an organ-at-risk, OAR, receive dose less than or equal to $\alpha_k$ PrDose. In treatment plan modeling module 24 and global optimization module 22, the cardinality of the index set K is between 3 and 10.

$$\sum_{i \in \beta} \sum_{i \in N_i} D_{P_{ij}} w_{ij} \leq [\alpha_k PrDose] y_P^{\alpha_k} + D_{max} z_P^{x_k}, \quad \text{Equation 15}$$
$$P \in OAR$$

$$\sum_{P \in OAR} y_P^{\alpha_k} \geq \beta_k |OAR| \quad \text{Equation 16}$$

$$y_P^{\alpha_k} + z_P^{\alpha_k} = 1 \quad \text{Equation 17}$$

$$y_P^{\alpha_{k1}} \leq y_P^{\alpha_{k2}} \text{ for } \alpha_{k_1} \leq \alpha_{k_2} \quad \text{Equation 18}$$

Here, $D_{max}$ is the maximum dose tolerance allowed for OAR, and $\alpha_k, \beta_k$ combinations are patient and tumor specific.

There are many objective functions that can be used to drive the optimization engine. For the computational work in this example, the objective was to minimize a weighted sum of the excess dose to the PTV and the total dose to organs-at-risk. Of course, other objectives may be employed.

The MIP instances include the basic dosimetric and volumetric constraints as described in Equations 10–18 in addition to other clinical constraints. The resulting MIP instances have at least $\Sigma_{i \in B}|N_i|+1+3(|PTV|+1)+\Sigma_{i \in O}|K|$ $(2|OAR_i|+1)+(|K|-1)|OAR_i|$ constraints; $\Sigma_{i \in B}|N_i|+|PTV|$ continuous variables; and $|B|+|PTV|+\Sigma_{i \in O}2|K||OAR_i|$ binary variables, where O is the set of all organs-at-risk and normal structures. For real patient cases, there are tens of thousands of variables and constraints. For such cases, the instances have proven to be computationally very difficult for competitive commercial MIP solvers. Following, a few specialized techniques that may be implemented in treatment plan modeling module 24 are described.

To maintain a tractable linear program relaxation, at a node of the branch-and-bound tree, instead of setting up the entire problem instance using all the voxel information, a master problem which consists of roughly half of the original voxels may be generated. This subset is selected carefully in order to maintain a realistic description of the problem. As the solution process proceeds, additional voxels are introduced. This leads to the addition of constraints and the corresponding columns (variables). Constraints which have remained inactive for a specified number of LP solves are removed from the master problem, thus providing a mechanism for controlling the size of the master instance.

For the constraint $\Sigma_{i \in B}x_i B_{max}$ which bounds the number of beams (gantry angles and directions) selected in the final plan, instead of branching on each binary variable with fractional value, global optimization module 22 branches on sets of binary variables. In particular, let $x^{LP}$ be the fractional solution. The branching scheme partitions B into $B_1 \cup B_2$ such that $\Sigma_{i \in B1} x_i^{LP}$ approximately equals $\Sigma_{i \in B2} x_i^{LP}$. In addition, an attempt is made to choose each set $B_i$ so that the included beams are roughly in the neighborhood of each other. Two new nodes are then created via the constraints $$\sum_{i \in B_1} x_i \leq \left\lfloor \frac{B_{max}}{2} \right\rfloor$$

and $$\sum_{i \in B_2} x_i \leq \left\lceil \frac{B_{max}}{2} \right\rceil.$$

The heuristic procedure is an LP-based primal heuristic in which at each iteration, some binary variables are set to 1 and the corresponding linear program is resolved. The procedure terminates when the linear program returns an integer feasible solution or when it is infeasible. In the former case, reduced-cost fixing is performed at the root node, as well as locally on each of the branch-and-bound nodes.

The heuristic procedure focuses on the binary variables $$q = (v_P, y_P^{\alpha_k}, z_P^{\alpha_k}) \quad \text{Equation 19}$$

from the constraints in Equations 12-18. Given a fractional solution obtained from an LP relaxation at a node, let $U=\{j: q_j^{LP}=1\}$, $F=\{j: 0<q_j^{LP}<1\}$, and $q^{max}=\max \{q_j^{LP}: j \in F\}$. The heuristic works by first setting all binary variables in U to 1. Next, any variable in F for which the fractional value exceeds $q^{max}-\in$ is set to 1, where $\in$ is a real number between 0 and 0.2 and is dynamically chosen with each fractional LP solution. Finally, it sets to 1 any variable corresponding to a voxel that is in a specified neighborhood of a voxel for which the associated binary variable was already set to 1 in the previous two steps. The final step is based on the premise that if a voxel satisfies a certain dose bound, then all voxels in its neighborhood should also satisfy the dose bound. The implementation involves a one-to-one mapping between the variables and the geometric locations of the associated voxels in a fixed 3D coordinate system.

As known in the art, a disjunctive argument may be used to develop valid inequalities for mixed integer programs. Disjunctive cuts have the appeal that they can be applied to general integer programs without requiring any knowledge of the facial structure of the underlying polyhedron. Below, one implementation of a disjunctive approach is described.

Consider the polyhedron $$P_{IP} = \text{conv}\{x \in \Re_+^n : \hat{A}x \leq \hat{b}, x_j \in \{0,1\}, j=1, \ldots, p\} \quad \text{Equation 20}$$

where $\hat{A}x \leq \hat{b}$ includes $Ax \leq b$ and the restrictions $x_j \leq 1$ for $j=1, \ldots, p$; $\hat{A} \in \Re^{\overline{m} \times n}$. Let $x^t \in \Re_+^n$ be a feasible solution of $\hat{A}x \leq \hat{b}$ such that $0 < x_i^t < 1$ for some $i \in \{1, \ldots, p\}$ and consider the pair of polyhedra $$P_{xi,0} = \{x \in \Re_+^n : \hat{A}x \leq \hat{b}, x_i = 0\}$$

$$P_{xi,1} = \{x \in \Re_+^n : \hat{A}x \leq \hat{b}, x_i = 1\} \quad \text{Equation 21}$$

Clearly $P_{IP} \supset P_{x_i} \equiv \text{conv}(P_{x_i,0} \cup P_{x_i,1})$. Assume that both $P_{x_i,0}$ and $P_{x_i,1}$ are nonempty (otherwise, $x_i$ can be eliminated). The following fact, which is motivated by results in Balas [4], forms the basis of our cut-generation procedure.

For example, the system defined by Equations 22–28 is infeasible if, and only if, $x^t \notin P_{x_i}$:

$$\hat{A}y - \hat{b}y_0 \leq 0 \quad \text{Equation 22}$$

$$\hat{A}z - \hat{b}z_0 \leq 0 \quad \text{Equation 23}$$

$$z_i - z_o = 0 \quad \text{Equation 24}$$

$$y_i = 0 \quad \text{Equation 25}$$

$$z_o + y_o = 1 \quad \text{Equation 26}$$

$$z + y = x^t \quad \text{Equation 27}$$

$$y, z, y_o, z_o \geq 0 \quad \text{Equation 28}$$

This, together with Gale's Theorem of the Alternative, implies that $x^t \notin P_{x_i}$ if, and only if, the following linear system (Equations 29–34) is feasible:

$$\alpha + \beta^T x^t < 0 \quad \text{Equation 29}$$

$$u_1^T \hat{A} + u_4 e_i + \beta^T I \geq 0 \quad \text{Equation 30}$$

$$u_2^T \hat{A} + u_3 e_i + \beta^T I \geq 0 \quad \text{Equation 31}$$

$$-u_1^T \hat{b} + \alpha \geq 0 \quad \text{Equation 32}$$

$$-u_2^T \hat{b} - u_3 + \alpha \geq 0 \quad \text{Equation 33}$$

$$u_1, u_2 \geq 0 \quad \text{Equation 34}$$

where $u_1, u_2 \in \Re^{\overline{m}}$, $\beta \in \Re^n$, and $u_3, u_4, \alpha \in \Re$. From the latter system, form a linear program by (a) removing the first inequality and embedding it into the objective: min $\{\alpha + \beta^T x^t\}$, and (b) enforcing an appropriate bounding condition on $\alpha$. Such a linear program will be referred to as a disjunctive LP. If the optimal objective value of a disjunctive LP is negative, then the inequality $\beta^T x \geq -\alpha$ is a valid inequality for $P_{x_i}$ which cuts off the fractional solution $x^t$.

Empirical tests on the patient instances reveal that it is beneficial to generate cuts first based on the fractional variables $q = (v_P, y_P^{\alpha_k}, z_P^{\alpha_k})$. For each such 0/1 variable that satisfies $0.01 < q^t < 0.99$, we solve the corresponding disjunctive problem. In this exemplary implementation, $\|\beta\|_1 \leq 1$ ($l_1$ norm) is used as the bounding condition for $\alpha$. This cut-generation procedure may be performed at the root node, as well as at tree levels that are a multiple of 10 within the branch-and-bound tree. To avoid excessive computational time, we select pseudo-randomly only 10% of the fractional variables for cut generation.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

The invention claimed is:

1. A method for developing an optimal treatment plan for treatment of a target volume within a patient using an external beam radiation delivery unit, the method comprising:
    receiving information corresponding to at least one parameter related to intensity-modulated radiation therapy (IMRT) to be used in developing the optimal treatment plan;
    receiving information corresponding to at least one clinical objective related to a target volume and a critical structure;
    developing a treatment plan optimization model based on a plurality of variables corresponding to the at least one parameter related to IMRT and the at least one clinical objective which define a global system; and
    developing a globally optimal treatment plan which optimizes the at least one clinical objective subject to the at least one parameter.

2. The method of claim 1, further comprising providing a visual tool for enabling a user to evaluate the globally optimal treatment plan.

3. The method of claim 2, wherein the providing a visual tool comprises providing an isodose curve corresponding to the globally optimal treatment plan.

4. The method of claim 2, wherein the providing a visual tool comprises providing at least one of a dose-volume histogram, a coverage index, a conformity index, a homogeneity index, a tumor control and normal tissue complication probability index, and a display of clinical metrics to the user.

5. The method of claim 1, wherein the receiving the information corresponding to at least one parameter related to IMRT comprises receiving information corresponding to at least one of a beamlet fluence parameter, a field segments parameter, a couch angles parameter, a gantry angles parameter, and a plurality of beam geometry parameters.

6. The method of claim 1, further comprising receiving information corresponding to at least one constraint to be incorporated into the treatment plan optimization model.

7. The method of claim 6, wherein the receiving information corresponding to at least one constraint comprises receiving information corresponding to at least one of a dosimetric constraint and a beam geometry constraint.

8. The method of claim 7, wherein the developing a treatment plan optimization model is further based on the at least one constraint and the developing a globally optimal treatment plan comprises developing a globally optimal treatment plan which optimizes the at least one clinical objective subject to the at least one parameter and the at least one constraint.

9. The method of claim 1, wherein at least one of the plurality of variables is one of a 0/1 variable and a non-negative continuous variable.

10. The method of claim 1, wherein the developing a globally optimal treatment plan comprises:
defining a solution space according to a set of constraints; and determining the best solution within the solution space.

11. A system for optimizing treatment planning in intensity-modulation radiation therapy (IMRT), the system comprising:
a user interface for enabling a user to specify, at least one parameter related to IMRT, at least one constraint, and at least one clinical objective;
a treatment plan modeling module configured to develop a treatment plan optimization model containing a plurality of variables corresponding to the at least one parameter related to IMRT, the at least one constraint, and the at least one clinical objective; and
a global optimization module configured to calculate a globally optimal treatment plan which optimizes the at least one clinical objective subject to the at least one parameter related to IMRT and the at least one constraint.

12. The system of claim 11, further comprising a visual evaluation functionality that supports a visual tool for enabling a user to evaluate the globally optimal treatment plan.

13. The system of claim 12, wherein the visual evaluation functionality is configured to display an isodose curve corresponding to the globally optimal treatment plan.

14. The system of claim 12, wherein the visual evaluation functionality is configured to display a dose-volume histogram, a coverage index, a conformity index, a homogeneity index, a tumor control and normal tissue complication probability index, and a display of clinical metrics to the user.

15. The system of claim 11, wherein the user interface is configured to enable a user to specify at least one of a beamlet fluence parameter, a field segments parameter, a couch angles parameter, a gantry angles parameter, and a plurality of beam geometry parameters.

16. The system of claim 11, wherein the user interface is configured to enable a user to specify a candidate beam profile, at least one dose parameter, at least one clinical parameter, at least one clinical objective, at least one dosimetric constraint, and at least one beam geometry constraint.

17. The system of claim 11, wherein the treatment plan modeling module is configured to develop a treatment plan optimization model containing at least one 0/1 variable.

18. The system of claim 11, wherein the global optimization module is further configured to define a solution space according to a set of constraints and determine the best solution within the solution space.

19. A system for optimizing treatment planning in intensity-modulation radiation therapy (IMRT), the system comprising:
means for interfacing with an I/O device to enable a user to specify at least one parameter related to IMRT, at least one constraint, and at least one clinical objective;
means for modeling a global system based on a plurality of variables corresponding to the at least one parameter related to IMRT, the at least one constraint, and the at least one clinical objective; and
means for calculating a globally optimal treatment plan which optimizes the at least one clinical objective subject to the at least one parameter related to IMRT and the at least one constraint.

20. A computer program embodied in a computer-readable medium for optimizing treatment planning in intensity-modulation radiation therapy (IMRT), the computer program comprising:
logic configured to interface with a user and enable the user to specify at least one parameter related to IMRT, at least one constraint, and at least one clinical objective;
logic configured to develop a treatment plan optimization model containing a plurality of variables corresponding to the at least one parameter related to IMRT, the at least one constraint, and the at least one clinical objective; and
logic configured to calculate a globally optimal treatment plan which optimizes the at least one clinical objective subject to the at least one parameter related to IMRT and the at least one constraint.

21. The computer program of claim 20, further comprising a logic configured to provide a visual tool for enabling a user to evaluate the globally optimal treatment plan.

22. The computer program of claim 21, wherein the logic configured to provide a visual tool comprises logic configured to display at least one of the following to a user: an isodose curve corresponding to the globally optimal treatment plan, a dose-volume histogram corresponding to the globally optimal treatment plan, a coverage index corresponding to the globally optimal treatment plan, a conformity index corresponding to the globally optimal treatment plan, a homogeneity index corresponding to the globally optimal treatment plan, a tumor control and normal tissue complication probability index corresponding to the globally optimal treatment plan, and a display of clinical metrics corresponding to the globally optimal treatment plan.

23. The computer program of claim 20, wherein the logic configured to interface comprises logic configured to enable a user to specify at least one of a beamlet fluence parameter, a field segments parameter, a couch angles parameter, a gantry angles parameter, and a plurality of beam geometry parameters.

24. The computer program of claim 20, wherein the logic configured to interface comprises logic configured to enable a user to specify a candidate beam profile, at least one dose parameter, at least one clinical parameter, at least one clinical objective, at least one dosimetric constraint, and at least one beam geometry constraint.

25. The computer program of claim 20, wherein the logic configured to develop a treatment plan optimization model comprises logic configured to develop a treatment plan optimization model containing at least one 0/1 variable.

26. The computer program of claim 20, wherein the logic configured to calculate a globally optimal treatment plan comprises logic configured to define a solution space according to a set of constraints and determine the best solution within the solution space.

* * * * *